US012251424B2

(12) United States Patent
Eichenbaum et al.

(10) Patent No.: US 12,251,424 B2
(45) Date of Patent: Mar. 18, 2025

(54) METHODS OF PROTECTING VASCULAR INTEGRITY INDUCED BY TARGETED RADIATION THERAPY

(71) Applicant: Janssen Pharmaceutica NV, Beerse (BE)

(72) Inventors: Gary Eichenbaum, Belle Mead, NJ (US); Alfred Tonelli, Upper Nyack, NY (US)

(73) Assignee: Janssen Pharmaceutica NV, Beerse (BE)

( * ) Notice: Subject to any disclaimer, the term of this patent is extended or adjusted under 35 U.S.C. 154(b) by 672 days.

(21) Appl. No.: 16/633,854

(22) PCT Filed: Jul. 26, 2018

(86) PCT No.: PCT/US2018/043821
§ 371 (c)(1),
(2) Date: Jan. 24, 2020

(87) PCT Pub. No.: WO2019/023418
PCT Pub. Date: Jan. 31, 2019

(65) Prior Publication Data
US 2020/0164039 A1  May 28, 2020

Related U.S. Application Data

(60) Provisional application No. 62/537,049, filed on Jul. 26, 2017.

(51) Int. Cl.
*A61K 38/19* (2006.01)
*A61K 47/60* (2017.01)
*A61N 5/10* (2006.01)

(52) U.S. Cl.
CPC ............ *A61K 38/196* (2013.01); *A61K 47/60* (2017.08); *A61N 5/10* (2013.01); *A61N 2005/1094* (2013.01)

(58) Field of Classification Search
None
See application file for complete search history.

(56) References Cited

U.S. PATENT DOCUMENTS

| | | | |
|---|---|---|---|
| 5,869,451 A | 2/1999 | Dower | |
| 6,660,843 B1 | 12/2003 | Feige | |
| 7,091,311 B2 | 8/2006 | Dower | |
| 7,576,056 B2 | 8/2009 | MacDonald | |
| 7,615,533 B2 | 11/2009 | Yurkow | |
| 8,227,422 B2 | 7/2012 | Dower | |
| 2003/0158116 A1 | 8/2003 | Dower | |
| 2005/0137133 A1 | 6/2005 | MacDonald | |
| 2006/0040866 A1 | 2/2006 | MacDonald | |
| 2006/0210542 A1 | 9/2006 | Yurkow | |
| 2007/0148091 A1 | 6/2007 | Dower | |
| 2008/0119384 A1 | 5/2008 | Yurkow | |
| 2009/0311344 A1 | 12/2009 | Yurkow | |
| 2012/0070434 A1 | 3/2012 | Springhorn | |
| 2014/0047572 A1 | 2/2014 | Chen | |
| 2014/0051631 A1 | 2/2014 | Porteu | |
| 2020/0237871 A1 | 7/2020 | Gary | |
| 2022/0168392 A1 | 6/2022 | Gary | |

FOREIGN PATENT DOCUMENTS

| | | |
|---|---|---|
| JP | 10507776 A | 7/1998 |
| JP | 2001505898 A | 5/2001 |
| JP | 2007504132 A | 3/2007 |
| JP | 2012518408 A | 8/2012 |
| JP | 2012250880 | 12/2012 |
| JP | 201497958 A | 5/2014 |
| WO | 199325221 | 12/1993 |
| WO | 199417784 | 10/1994 |
| WO | 9640750 | 12/1996 |
| WO | 9640750 A1 | 12/1996 |
| WO | 9825965 | 6/1998 |
| WO | 9825965 A2 | 6/1998 |
| WO | 2004026332 A1 | 4/2004 |
| WO | 2005023834 | 3/2005 |
| WO | 2005023834 A2 | 3/2005 |
| WO | 2007021572 | 2/2007 |
| WO | 2007087428 | 8/2007 |
| WO | 2007087428 A2 | 8/2007 |
| WO | 2007094781 | 8/2007 |
| WO | 2008070583 | 6/2008 |
| WO | 2009114725 A2 | 9/2009 |
| WO | 2009148954 | 12/2009 |
| WO | 2010099019 A1 | 9/2010 |
| WO | 2014028509 | 2/2014 |

OTHER PUBLICATIONS

Pirker et al. ("Anemia in lung cancer: clinical impact and management" Clin Lung Cancer. Sep. 2003, 5(2):90-7).*
Li et al. ("Stereotactic ablative radiotherapy (SABR) using Gy in 10 fractions for non-small cell lung cancer: Explorations of clinical indications" Radiotherapy and Oncology vol. 112(2) Aug. 2014, pp. 256-261).*
Georgiou et al. ("Severe and Fatal Multilobar Nonclassic Radiation Pneumonitis following Stereotactic Body Radiation Therapy (SBRT) for Treatment of Inoperable Non-Small Cell Lung Cancer: A Report of Two Cases and Possible Enhancement by Concurrent Amiodarone" Case Rep Pulmonol. 2019).*
Liauw et al. ("New paradigms and future challenges in radiation oncology: an update of biological targets and technology" Science Translational Medicine; Feb. 20, 2013 vol. 5 (173).*
Berthelot-Richer et al. "Romiplostim efficacy in an acute myeloid leukemia patient with transfusion refractory thrombocytopenia", Transfusion. Apr. 2012;52(4):739-41 (Year: 2012).

(Continued)

*Primary Examiner* — Julie Ha
*Assistant Examiner* — Tara L Martinez
(74) *Attorney, Agent, or Firm* — Ice Miller LLP

(57) ABSTRACT

Methods of protecting vascular integrity in a subject exposed to a targeted radiation therapy are described. In particular, an effective amount of a thrombopoietin (TPO) mimetic, such as TPOm, is used to protect vascular integrity following the radiation therapy.

21 Claims, 13 Drawing Sheets

Specification includes a Sequence Listing.

(56) References Cited

OTHER PUBLICATIONS

Liem-Moolenaar et al. "Pharmacodynamics and Pharmacokinetics of the Novel Thrombopoietin Mimetic Peptide RWJ-800088 in Humans". Clin Pharmacol Ther. Oct. 2008; 84(4):481-7 (Year: 2008).
"Highlights of Prescribing Information". FDA. Rev. Dec. 2011. [online][accessed from www.accessdata.fda.gov/drugsatfda_docs/label/ 2011/125268s077lbl.pdf] (Year: 2011), 14 pages.
Fenaux et al. "Romiplostim monotherapy in thrombocytopeniatients with myelodysplastic syndromes: long-term safety and efficacy". British Journal of Haematology, 2017, 178, 906-913. (Year: 2017).
Fang Chen et al, "Effect of radiation-induced endothelial cell injury on platelet regeneration by megakaryocytes", Journal of Radiation Research, JP, (Jul. 1, 2017), vol. 58, No. 4, doi:10.1093/jrr/rrx015, ISSN 0449-3060, pp. 456-463, XP055514757.
Yamaguchi Masaru et al, "The thrombopoietin mimetic romiplostim leads to the complete rescue of mice exposed to lethal ionizing radiation", vol. 8, doi:10.1038/S41598-018-29013-5, ISSN 2045-2322, (Jul. 13, 2018), pp. 1-12, Scientific Reports,, URL: http://www.nature.com/srep, (May 4, 2020), XP009513711.
Ashcraft K A et al, "Application of a Novel Murine Ear Vein Model to Evaluate the Effects of a Vascular Radioprotectant on Radiation-Induced Vascular Permeability and Leukocyte Adhesion", vol. 190, No. 1, (Jul. 1, 2018), pp. 12-21, Radiation Research.
Baker et al., Cancer Invest., 1989, 7:287-94.
Baker et al., Cardiovasc. Res. 77(1):44-53 (2008).
Birer et al., Radiation Research, 188(1):94-104 (2017).
Brush et al., Semin. Radiat. Oncol. 17(2):121-30 (2007).
Chan et al., Eur. J. Heart Fail. 13(4):366-76 (2011).
Gaither et al., The Journal of Sexual Medicine, 2017, 14(9):1071-8.
Hallahan et al., Biochem. Biophys. Res. Commun. 217(3):784-95 (1995).
Hallahan et al., Radiat. Res. 152(1):6-13 (1999)).
Kalman et al., Int. J. Radiat. Oncol. Biol. Phys., 2017, 98:662-682.
Kim et al., Radiat. Oncol. J. 32(3):103-15 (2014).
Knight et al., Int. J. Toxicol. 30(4):385-404(2011).
Krigsfeld et al., Radiat. Res. 180(3): 231-4 (2013).
Langer et al., J. Mol. Cell Cardiol. 47(2):315-25 (2009).
Li et al., Blood 98(12):3241-8 (2001).
Mitchell and Bussell, Semin. Hematol. 52(1):46-52 (2015).
Mouthon et al., Can. J. Physiol. Pharmacol. 80(7):717-21 (2002).
Neelis et al., Blood 90(7):2565-73 (1997).
Nolan et al., Int J Radiat Oncol Biol Phys. 2015, 91(4):796-806.
Park et al., Radiation Research: Mar. 2012, vol. 177, No. 3, pp. 311-327.
Rotolo et al., J. Clin. Invest. 122(5):1786-90 (2012).
Waselenko et ah, Ann. Intern. Med. 140(12): 1037-51 (2004).
Zhou et al., J. Cereb Blood Flow Metab. 31(3):924-33 (2011).
International Search Report and Written Opinion issued in PCT/US2018/043821, 12 pages.
International Preliminary Report on Patentability issued in PCT/US2018/043821, 8 pages.
Kuter, DJ. "The biology of thrombopoietin and thrombopoietin receptor agonists". Int J Hematol (2013) 98:10-23. (Year: 2013).
Yamaguchi, M., et al., Thrombopoietin-Mimetic Romiplostim Confers the Complete Survival Rate to Mice Exposed to Lethal Ionizing Radiation. Blood 2015; 126 (23): 2390.

* cited by examiner

METHODS OF PROTECTING VASCULAR INTEGRITY INDUCED BY TARGETED RADIATION THERAPY

CROSS-REFERENCE TO RELATED APPLICATIONS

This application is a Section 371 of International Application No. PCT/US18/43821, filed Jul. 26, 2018, which was published on Jan. 31, 2019, under International Publication No. WO 2019/023418 A1, which claims priority U.S. Patent Application No. 62/537,049, filed Jul. 26, 2017, the disclosures of each of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing", creation date of Jul. 24, 2018, and having a size of about 3.7 kb. The sequence listing submitted via EFS-Web is part of the specification and is herein incorporated by reference in its entirety.

FIELD OF THE INVENTION

This invention relates to methods of protecting vascular integrity, more specifically, methods of protecting vascular integrity in a subject exposed to a targeted radiation therapy. The methods comprise administering to the subject an effective amount of a thrombopoietin (TPO) mimetic.

BACKGROUND OF THE INVENTION

Acute radiation syndrome (ARS), also known as radiation toxicity or radiation sickness, is an acute illness caused by irradiation of the entire body (or most of the body) by a high dose of penetrating radiation in a very short period of time. It is a multi-phasic process that can lead to morbidity and mortality (Waselenko et al., Ann. Intern Med. 140(12):1037-51 (2004)). Immediate effects of irradiation are seen within the vasculature followed by pronounced hematopoietic effects (Krigsfeld et al., Radiat. Res. 180(3): 231-4 (2013)). Within 24 hours after irradiation, vascular endothelial cells express adhesion molecules (e.g. L-selectin), which promotes leukocyte adhesion and extravasation, and can lead to an inflammatory response (Hallahan et al., Biochem. Biophys. Res. Commun. 217(3):784-95 (1995); Hallahan et al., Radiat. Res. 152(1):6-13 (1999)). These early vascular effects may be accompanied by exposure of the basement membrane and hemorrhage, which then leads to microclot formation. Depending on the extent of microclot formation, this may then lead to platelet and fibrinolytic factor depletion. Because the platelet population cannot be efficiently replenished due to irradiation depletion of hematopoietic stem cells, thrombocytopenia ensues, leading to further vascular thinning and a progression to disseminated intravascular coagulopathy. Therefore, protection of the vascular endothelium may mitigate radiation-induced injury and mortality (Rotolo et al., J. Clin. Invest. 122(5):1786-90 (2012)).

The pathogenesis leading to injury to surrounding normal tissue following radiation exposure is complex. Ionizing radiation causes cell death, both parenchymal and vascular, through direct cytotoxicity (excessive generation of reactive oxygen species), inflammation, and the innate immune response (Kim et al., Radiat. Oncol. J. 32(3):103-15 (2014)). Some changes occur acutely, (i.e., inflammation, vascular endothelial injury, micro-hemorrhage) while others manifest weeks to months after radiation exposure (i.e., chronic inflammation, nerve dysfunction, scarring and fibrosis). Fibroblast proliferation is a key component of later stage Radiation therapy (RT) injury (Brush et al., Semin. Radiat. Oncol. 17(2):121-30 (2007)).

Given that multiple facets of radiation-induced morbidity and mortality stem from platelet depletion, several investigators have evaluated whether thrombopoietin (TPO)-based therapies are effective in preventing acute radiation syndrome (Mouthon et al., Can. J. Physiol. Pharmacol. 80(7): 717-21 (2002); Neelis et al., Blood 90(7):2565-73 (1997)). Potential mechanisms for the enhanced survival include its myeloprotective and platelet stimulatory effects as well as direct protective and/or reparative effects on vascular endothelium. Thrombopoietin (TPO) is a growth factor that is synthesized and secreted by the liver. TPO regulates platelet levels by binding to c-mpl on megakaryocytes (to stimulate platelet maturation) and existing platelets (providing negative feedback) (Mitchell and Bussell, Semin. Hematol. 52(1):46-52 (2015)). TPO may also act directly on vasculature by binding to c-mpl receptors located on vascular endothelial cells (Langer et al., J. Mol. Cell Cardiol. 47(2):315-25 (2009)). There have been several studies demonstrating direct vascular protective effects of thrombopoietin in animal models of doxorubicin mediated cardiovascular injury (Chan et al., Eur. J. Heart Fail. 13(4):366-76 (2011)), cardiovascular ischemia reperfusion injury (Baker et al., Cardiovasc. Res. 77(1):44-53 (2008)) and stroke (Zhou et al., J. Cereb Blood Flow Metab. 31(3):924-33 (2011)). Recombinant human TPO is not a viable therapy in humans, however, due to induction of cross-reactive antibodies to endogenous TPO that can lead to chronic thrombocytopenia (Li et al., Blood 98(12):3241-8 (2001)).

Considerable vascular damages can be induced by targeted radiation, such as high-dose stereotactic body radiotherapy (SBRT) or stereotactic radiosurgery (SRS) (Park et al., Radiation Research: March 2012, Vol. 177, No. 3, pp. 311-327). It is suggested that radiation-induced vascular damage may play an important role in the response of human tumors to high-dose targeted radiation, e.g., damages to the intratumor microenvironment may lead to indirect death of tumor cells. Id. However, many patients treated with targeted radiation develop side effects as a result of their treatment. For example, 90% of patients suffering from head and neck squamous cell carcinomas (HNSCC) treated with targeted radiotherapy with curative intent develop side effects, including dermatitis, xerostomia (loss of saliva production), and oral mucositis (inflammation and ulceration of the oropharyngeal and/or esophageal mucosa) (Birer et al., Radiation Research, 188(1):94-104 (2017)). Another example where vascular injury has been hypothesized to play a role following targeted radiation is in the context of erectile dysfunction following targeted irradiation of the prostate for the treatment of prostate cancer. (Gaither et al., The Journal of Sexual Medicine, 2017, 14(9):1071-8 and Nolan et al., Int J Radiat Oncol Biol Phys. 2015, 91(4):796-806). The effect of TPO or TPO mimetics on vascular changes induced by targeted radiation therapy has not been reported.

There exists an important and unmet need for methods and compositions that provide protection of normal tissues following radiation therapy.

BRIEF SUMMARY OF THE INVENTION

It is surprisingly discovered in the present invention that a thrombopoietin (TPO) mimetic protects the vasculature and preserves vascular integrity in the normal tissues following targeted radiation therapy. Accordingly, provided herein are methods of protecting vascular integrity in a subject exposed to a targeted radiation therapy. The methods comprise administering to the subject exposed to a targeted radiation therapy an effective amount of a thrombopoietin (TPO) mimetic, preferably the TPO mimetic comprises the amino acid sequence of SEQ ID NO:1, more preferably the TPO mimetic is RWJ-800088 or romiplostim. According to embodiments of the application, the TPO mimetic is administered at least about 10 minutes to at least about 420 minutes after the subject is exposed to the targeted radiation therapy, more preferably, the TPO mimetic is TPOm having the following structure of formula (I), or a pharmaceutically acceptable salt or ester thereof:

In certain embodiments, the effective amount of the TPO mimetic is administered to the subject by intravenous, intramuscular, intracutaneous, or subcutaneous injection. In preferred embodiments, the TPO mimetic is administered by subcutaneous injection.

In another general aspect, the application relates to a kit for preserving vascular integrity in a subject in need thereof. The kit comprises a pharmaceutical composition comprising an effective amount of a TPO mimetic and a pharmaceutically acceptable carrier, and at least one additional therapeutic agent or device for preserving vascular integrity. Optionally, the kit further comprises a tool for administering the TPO mimetic to the subject. Preferably, the kit comprises a TPO mimetic having the amino acid sequence of SEQ ID NO:1, more preferably the TPO mimetic of RWJ-800088 or romiplostim.

Formula (I)

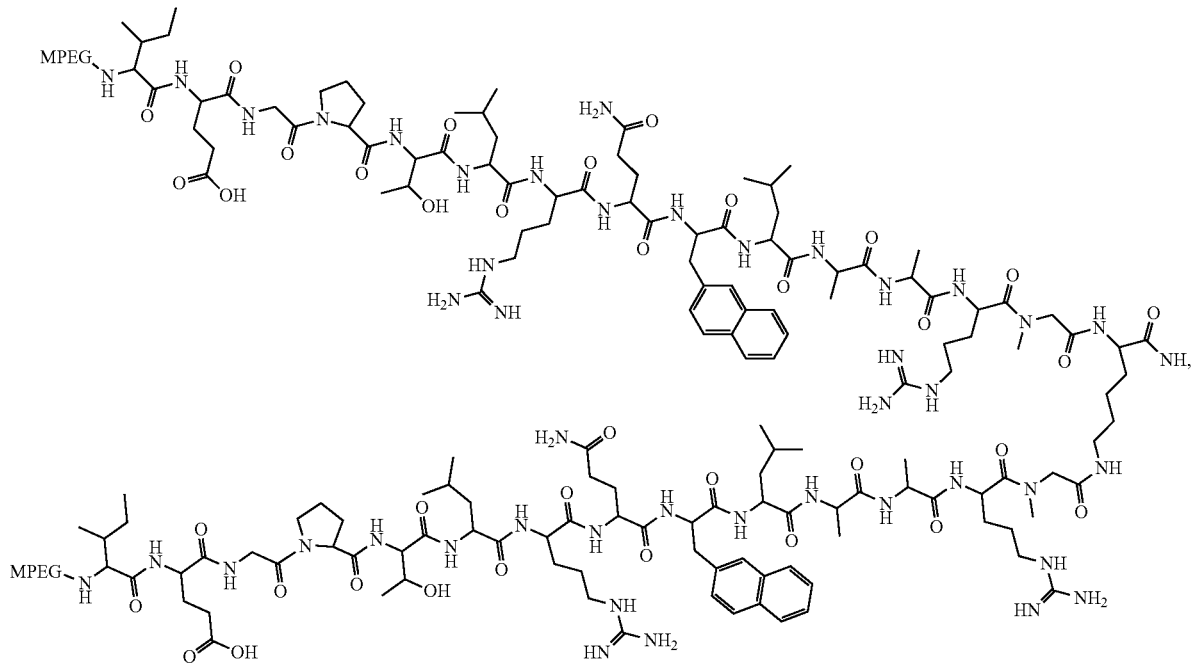

wherein MPEG represents methoxypolyethylene glycol or methoxypoly(ethylene glycol); and wherein administration of an effective amount of the TPO mimetic to the subject protects the vascular integrity of the subject.

In certain embodiments, the subject exposed to targeted radiation therapy is being treated for cancer. The cancer can, for example, be selected from the group consisting of prostate cancer, head and neck cancer, hepatocellular carcinoma, colon cancer, lung cancer, melanoma, and breast cancer.

In certain embodiments, the TPO mimetic is administered to the subject at least about 20 minutes to at least about 360 minutes, at least about 40 minutes to at least about 240 minutes, at least about 60 minutes to at least about 180 minutes, or any amount in between, after the subject is exposed to the targeted radiation therapy.

In certain embodiments, the subject is administered one dose of the effective amount of the TPO mimetic.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings. As used in FIGS. 1 to 10, "TPOm" refers to RWJ-800088.

FIG. 1 shows the average rat weights by treatment following 20 Gy targeted radiation treatment (RT) to the prostate.

FIG. 3 shows that TPOm protects vasculature outside of the radiation field.

FIG. 5 shows the scheme for extraction of time activity curves (TAC), demonstrated using a mouse in the RT+TPOm arm.

FIG. 9 shows leukocyte/endothelial cell interactions, assessed using acridine orange intravital microscopy.

DETAILED DESCRIPTION OF THE INVENTION

Figure 1A:
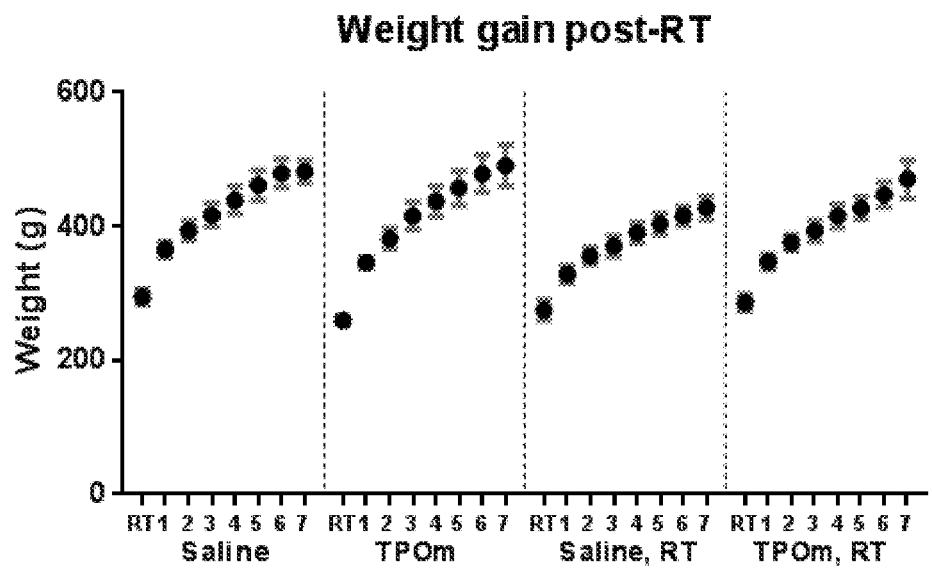
FIG. 1A shows a graph demonstrating that all rats continued to gain weight following radiation, regardless of treatment.

This disclosure is based upon, at least in part, on the identification of a thrombopoietin (TPO) mimetic as a therapeutic for protecting vascular integrity in subjects exposed to a targeted radiation therapy. The TPO mimetic can be formulated and administered to subjects exposed to a targeted radiation therapy to protect against the negative effects of the radiation on the vasculature, particularly the vasculature of healthy tissues, of the subject.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human, to whom will be or has been vaccinated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right", "left", "lower" and "upper" designate directions in the drawings to which reference is made.

As used herein, the term "in combination", in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The term "protecting vascular integrity," as used herein, refers to preserving and maintaining at least one of the functions and structures of the vascular system in a subject following RT. A primary function of the vascular system is to carry blood and lymph throughout the body of the subject, delivering oxygen and nutrients and taking away tissue waste matter. The term "protecting vascular integrity" can refer to preserving or maintaining the function of the vascular system such that the circulation of blood and lymph throughout the body is not affected or altered significantly upon exposure to the targeted radiation therapy. The term "protecting vascular integrity" can also refer to preserving or maintaining one or more other functions of the vascular system, such as protecting the subject from impaired pudendal artery vasodilation following RT, or reducing vasoconstriction following RT. The vascular system is composed of blood vessels (e.g., arteries, veins, and capillaries) and lymph vessels that circulate the blood and lymph, respectively, throughout the body. Structurally, blood vessels are composed of an outer endothelium layer and three tissue layers; the tunica externa, the tunica media, and the tunica intima. The term "protecting vascular integrity" can further refer to preserving or maintaining the structure of the vascular system such that the structure of the vascular system is not altered or affected significantly following radiation therapy, for example, there is no substantial vascular leakage or substantial increase in vascular endothelial leukocyte interaction following the RT.

Targeted Radiation Therapy

The term "RT", "TRT" or "targeted radiation therapy", as used herein, refers to a therapy using ionizing radiation that is preferentially targeted or localized to a specific organ or part of the body. It is generally used as part of cancer treatment. Targeted radiation therapy (TRT) is sometimes also referred to as radiation treatment, radiotherapy, irradiation, or x-ray therapy. There are three main divisions of targeted radiation therapy: external beam radiation therapy (EBRT or XRT), internal radiation therapy, and systemic radioisotope therapy. Sometime, the radiation can be given in several treatments to deliver the same or slightly higher dose, which is called fractioned radiation therapy.

External beam radiation therapy (EBRT) uses a machine that directs high-energy rays from outside the body into the tumor. Examples of EBRT include, but are not limited to, stereotactic radiation therapy, image guided radiation therapy (IGRT), intensity modulated radiation therapy (IMRT), helical-tomotherapy, proton beam radiation therapy, and intraoperative radiation therapy (IORT).

Internal radiation is also called brachytherapy, in which a radioactive implant is put inside the body in or near the tumor. It allows a higher dose of radiation in a smaller area than might be possible with external radiation treatment. It uses a radiation source that's usually sealed in a small holder called an implant. Different types of implants may be called pellets, seeds, ribbons, wires, needles, capsules, balloons, or tubes. One such example of internal radiation is transarterial chemoembolization (TACE).

Systemic radioisotope therapy (SRT) is also called unsealed source radiotherapy. Targeted radioactive drugs are used in SRT to treat certain types of cancer systemically, such as thyroid, bone, and prostate. These drugs, which are typically linked to a targeting entity—such as a monoclonal antibody or a cell-specific ligand, can be given by mouth or put into a vein; they then travel through the body until reaching at the desired target, where the drug will accumulate in a relatively high concentration.

In one embodiment, the invention relates to a targeted radiation therapy for treating a head and neck cancer. A typical course of radiation for cancer of the head and neck lasts 3-5 weeks with daily treatments. However, rapidly growing cancers are poorly controlled if radiation is given in daily doses over a long period of time. Therefore, delivery of radiation can be accelerated and given in two or more treatments per day (hyperfractionation) for certain rapidly growing head and neck cancers, such as nasopharyngeal cancers. In some embodiments, a subject with cancer of the head and neck is treated with higher doses of radiation therapy that are administered twice daily compared to standard therapy consisting of lower doses administered once a day.

EBRT and/or brachytherapy are commonly used for head and neck radiation treatment. For example, removable implants can be used in the treatment of cancers of the mouth, tongue, throat, and nasopharynx where they are given as intracavitary boosts following external beam radiation therapy. The implants are placed in the area of the cancer and removed when the appropriate dose is administered. The most commonly used radioactive substance in removable implants is iridium 192. In some embodiments, permanent placement of radioactive sources can be necessary, for example, in the treatment of recurrent nasophayngeal malignancies, for palliation of accessible recurrences of primary sites in the mouth and throat, or for cervical lymph node metastases. Iodine 125 and palladium 103 can be the radioactive substances used for permanent implants.

Side effects of targeted radiation for head and neck cancers include, for example, mucositis, inflammation of the mucous membranes of the mouth or throat, or dry mouth (xerostomia). Another frequently encountered complication of radiation therapy for head and neck cancer is abnormally low levels of thyroid hormone, referred to as hypothyroidism.

In another embodiment, the invention relates to a targeted radiation therapy for treating a prostate cancer. EBRT and high-dose rate (HDR) brachytherapy are the two primary types of radiation therapy for the treatment of prostate cancer. Side effects of targeted radiation for prostate cancer include, for example, frequent urination, difficult or painful urination, blood in urine, urinary leakage, painful bowel movements, rectal bleeding, and sexual dysfunction, such as erectile dysfunction.

TPO Mimetic

As used herein, a "TPOm", "TPO mimetic" or "thrombopoietin mimetic" refers to a compound comprising a peptide capable of binding to and activating a thrombopoietin receptor. Preferably, in a TPO mimetic useful for the invention, the peptide capable of binding to and activating a thrombopoietin receptor has no significant homology with thrombopoietin (TPO). The lack of homology with TPO reduces the potential for generation of TPO antibodies. Examples of such peptide useful in a TPO mimetic include, but are not limited to, those described in U.S. Publication Nos. 2003/0158116; 2005/0137133; 2006/0040866; 2006/0210542; 2007/0148091; 2008/0119384; U.S. Pat. Nos. 5,869,451; 7,091,311; 7,615,533; 8,227,422; International Patent Publications WO2007/021572; WO2007/094781; and WO2009/148954, the entire contents of which are incorporated herein by reference. More preferably, in a TPO mimetic useful for the invention, the peptide capable of binding to and activating a thrombopoietin receptor is covalently linked to a moiety that improves one or more properties of the peptide. By way of a non-limiting example, the moiety can be a hydrophilic polymer, including but not limited to polyethylene glycol (PEG), polypropylene glycol, polylactic acid and polyglycolic acid. The moiety can also be a polypeptide, such as a Fc region or an albumin.

In a preferred embodiment, a TPO mimetic useful for the invention comprises a peptide having the amino acid sequence of: IEGPTLRQXaaLAARYaa (SEQ ID NO:1), wherein Xaa is tryptophan (W) or β-(2-naphthyl)alanine (referred to herein as "2-Nal"), and Yaa is alanine (A) or sarcosine (referred herein as "Sar"). Preferably, the peptide of SEQ ID NO:1 is covalently linked to a PEG or fused to a Fc domain.

In some embodiments, a TPO mimetic useful for the invention comprises a peptide of SEQ ID NO:1 covalently linked to a PEG, preferably a PEG having an average molecular weight of between about 5,000 to about 30,000 daltons. Preferably, the PEG is selected from the group consisting of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM). The PEGylation of the peptide leads to a reduced clearance of the compound without loss of potency. See, e.g., U.S. Pat. No. 7,576,056, the entire contents of which are incorporated herein by reference.

In one preferred embodiment, a TPO mimetic useful for the invention is RWJ-800088 or a derivative thereof. As used herein, "RWJ-800088" refers to a 29-mer peptide having two identical 14-mers linked by a lysinamide residue as follows:

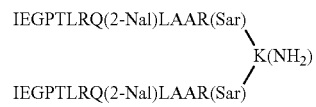

and having a methoxypoly(ethylene glycol) (MPEG) covalently linked to each N-terminal isoleucine, or a pharmaceutically acceptable salt or ester thereof. The 14-mers is identical to SEQ ID NO:1, wherein Xaa is 2-Nal and Yaa is Sar, The RWJ-800088 is thus composed of two 14 amino acid peptide chains of SEQ ID NO:2 (IEGPTLRQ(2-Nal)LAAR(Sar)) linked by lysinamide reside, and each N-terminal isoleucine is linked to a methoxy polyethylene glycol (MPEG) chain. Accordingly, RWJ-800088 has an abbreviated molecular structure of (MPEG-Ile-Glu-Gly-Pro-Thr-Leu-Arg-Gln-(2-Nal)-Leu-Ala-Ala-Arg-(Sar))$_2$-Lys-NH$_2$; wherein (2-Nal) is β-(2-naphthyl)alanine, (Sar) is sarcosine and MPEG is methoxypoly(ethylene glycol), or a pharmaceutically acceptable salt or ester thereof. Preferably, the MPEG has an approximately 20,000 Dalton molecular weight or represents methoxypolyethylene glycol20000.

In one embodiment, RWJ-800088 has a molecular structure of formula (I), or a pharmaceutically acceptable salt or ester thereof:

```
                                                        (SEQ ID NO: 4)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ
```

Formula (I)

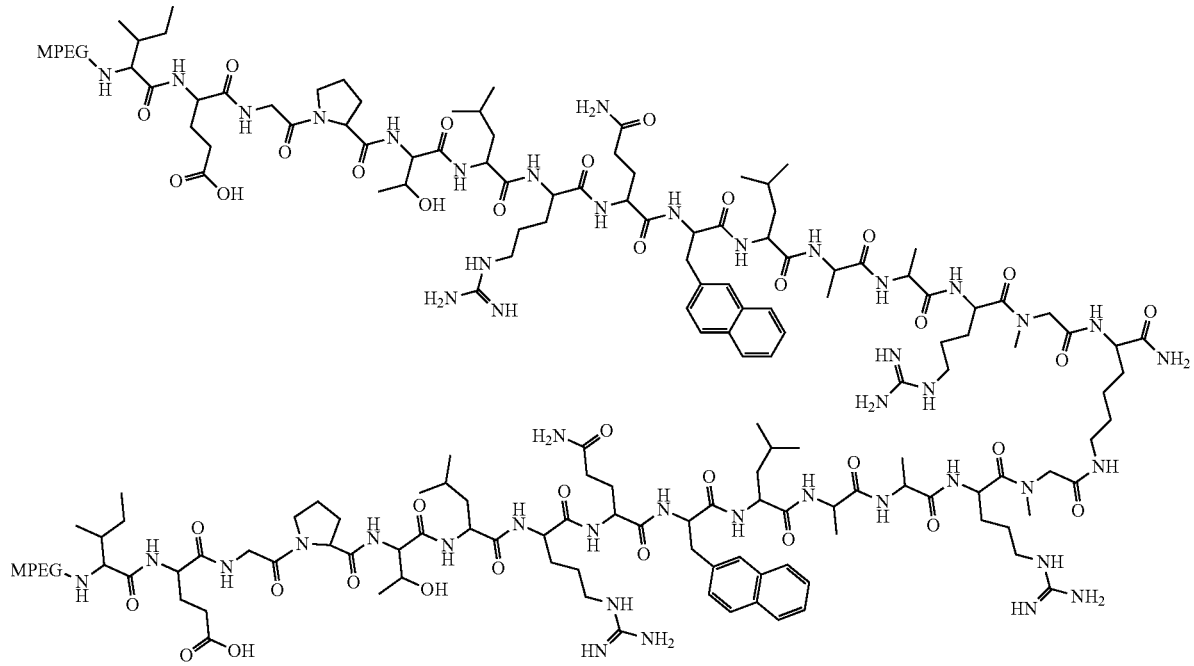

In a preferred embodiment, the MPEG in RWJ-800088 is methoxypolyethyleneglycol20000, and the RWJ-800088 has the full chemical name of: methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-Nε-(methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-)-Lysinamide, or a pharmaceutically acceptable salt or ester thereof. The molecular weight of the peptide without PEG is 3,295 Daltons and with two 20,000 Dalton MPEG chains is approximately 43,295 Daltons.

In some embodiments, a TPO mimetic useful for the invention comprises a peptide of SEQ ID NO:1 fused to a Fc domain. Fusing the peptide to a Fc domain can stabilize the peptide in vivo. See, e.g., U.S. Pat. No. 6,660,843, the entire contents of which are incorporated herein by reference.

In another preferred embodiment, a TPO mimetic useful for the invention is romiplostim. As used herein, "romiplostim" refers to fusion protein having a Fc domain linked to the N-terminal isoleucine of the peptide of SEQ ID NO:1, where Xaa is W and Yaa is A. In particular, romiplostim has the following amino acid sequence:

-continued
```
QGNVFSCSVMHEALHNHYTQKSLSLSPGKGGGGGIEGPTLRQWLAARAGG

GGGGGGIEGPTLRQWLAARA,
```

It has the thrombopoietin receptor binding domain amino acid sequence of IEGPTLRQWLAARA (SEQ ID NO:3).

Dosage and Administration

The TPO mimetic can, for example, be administered as an active ingredient of a pharmaceutical composition in association with a pharmaceutical carrier or diluent. The TPO mimetics can be administered by oral, pulmonary, parental (intramuscular, intraperitoneal, intravenous (IV) or subcutaneous injection), inhalation (via a fine powder formulation), transdermal, nasal, vaginal, rectal, or sublingual routes of administration can be formulated in dosage forms appropriate for each rout of administration. See, e.g., International Publication Nos. WO1993/25221 (Bernstein et al.) and WO1994/17784 (Pitt et al.), the relevant content of which is incorporated herein by reference.

Solid dosage forms for oral administration include capsules, tablets, pills, powders, and granules. In such solid dosage forms, the active peptide compound is admixed with at least one pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through bacteria retaining filter, by incorporating sterilizing agents into the compositions, by irradiating the compositions, or by heating the compositions. They can also be manufactured using sterile water, or some other sterile injectable medium immediately before use.

Administration of the TPO mimetic is typically intramuscular, subcutaneous, or intravenous. However other modes of administration such as cutaneous, intradermal or nasal can be envisaged as well. Intramuscular administration of the TPO mimetic can be achieved by using a needle to inject a suspension of the TPO mimetic composition. An alternative is the use of a needleless injection device to administer the composition (using, e.g., Biojector™) or a freeze-dried powder of the TPO mimetic composition.

For intravenous, cutaneous or subcutaneous injection, or injection at the site of affliction, the TPO mimetic composition can be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Compositions for rectal or vaginal administration are preferably suppositories which may contain, in addition to the active TPO mimetic, excipients such as cocoa butter or a suppository wax. Compositions for nasal or sublingual administration are also prepared with standard excipients well known in the art.

Typically, administration will aim to maintain and protect vascular integrity against a targeted radiation therapy administered to the subject. The TPO mimetic compositions are administered to a subject during or after the targeted radiation treatment, and the TPO mimetic compositions are administered in an amount sufficient to protect the vascular integrity in healthy tissues of the subject, preferably without decreasing the efficacy of the RT.

The pharmaceutically acceptable compositions containing the TPO mimetic are administered to a subject, giving rise to protective effect on the vasculature of the subject. An amount of a composition sufficient to produce a protective effect on the vasculature of the subject is defined to be an "effective dose" or an "effective amount" of the composition. The effective amount of the TPO mimetic compositions will depend on, e.g., the state of the subject (e.g., severity of the vasculature integrity, length of exposure to targeted radiation therapy), the physical characteristics of the subject (e.g., height, weight, etc.), and the nature of the RT (e.g., type and dose of radiation, frequency, etc.). The actual amount administered and rate and time-course of administration can be determined by one skilled in the art in view of the present disclosure.

Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

In certain embodiments, the TPO mimetic is administered to the subject at least about 10 minutes to at least about 420 minutes, at least about 10 minutes to at least about 300 minutes, at least about 10 minutes to at least about 180 minutes, at least about 10 minutes to at least about 60 minutes, at least about 20 minutes to at least about 420 minutes, at least about 20 minutes to at least about 300 minutes, at least about 20 minutes to at least about 180 minutes, at least about 20 minutes to at least about 60 minutes, at least about 40 minutes to at least about 420 minutes, at least about 40 minutes to at least about 300 minutes, at least about 40 minutes to at least about 180 minutes, at least about 40 minutes to at least about 60 minutes, at least about 60 minutes to at least about 420 minutes, at least about 60 minutes to at least about 300 minutes, at least about 60 minutes to at least about 180 minutes, at least about 60 minutes to at least about 120 minutes, at least about 60 minutes to at least about 90 minutes, at least about 80 minutes to at least about 420 minutes, at least about 80 minutes to at least about 300 minutes, at least about 80 minutes to at least about 180 minutes, at least about 80 minutes to at least about 120 minutes, at least about 100 minutes to at least about 420 minutes, at least about 100 minutes to at least about 300 minutes, at least about 100 minutes to at least about 180 minutes, at least about 100 minutes to at least about 150 minutes, at least about 120 minutes to at least about 420 minutes, at least about 120 minutes to at least about 300 minutes, at least about 120 minutes to at least about 180 minutes, at least about 140 minutes to at least about 420 minutes, at least about 140 minutes to at least about 300 minutes, at least about 140 minutes to at least about 180 minutes, at least about 160 minutes to at least about 420 minutes, at least about 160 minutes to at least about 300 minutes, at least about 160 minutes to at least about 180 minutes, at least about 180 minutes to at least about 420 minutes, at least about 180 minutes to at least about 300, or any amount in between after the subject is exposed to the targeted radiation therapy. In certain embodiments, the TPO mimetic is administered at least about 10, at least about 20, at least about 40, at least about 60, at least about 80, at least about 100, at least about 120, at least about 140, at least about 160, at least about 180, at least about 200, at least about 220, at least about 240, at least about 260, at least about 280, at least about 300, at least about 320, or at least about 340 minutes after the subject is exposed to the targeted radiation therapy. In certain embodiments, the TPO mimetic is administered at least about 8, at least about 10, at least about 12, at least about 14, at least about 16, at least about 18, at least about 20, at least about 22, at least about 24 hours after the subject is exposed to the targeted radiation therapy. In certain embodiments, the TPO mimetic is administered no later than about 10, about 20, about 40, about 60, about 80, about 100, about 120, about 140, about 160, about 180, about 200, about 220, about 240, about 260, about 280, about 300, about 320, about 340, about 360, about 420 minutes after the subject is exposed to the targeted radiation therapy. In certain embodiments, the TPO mimetic is administered no later than about 8, about 10, about 12, about 14, about 16, about 18, about 20, about 22, about 24 hours after the subject is exposed to targeted radiation therapy.

Following production of the TPO mimetic and optional formulation of the TPO mimetic into compositions, the compositions can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of protecting vascular integrity due to administration of the TPO mimetic.

The TPO mimetic compositions of the invention can be administered alone or in combination with other treatments, either simultaneously or sequentially dependent upon the condition to be treated.

The TPO mimetic compositions can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration. The device included in the kit can be, for example, a container, a delivery vehicle, or an administration device.

The kit can further comprise at least one additional therapeutic agent or a device for protecting vascular integrity. The additional therapeutic agent included in the kit refers to any compound or therapeutic agent known to or that demonstrates advantageous properties when administered with TPO or a TPO mimetic. Examples of such agents can be, but are not limited to: other TPO mimetics, other agents that can be used to protect vascular integrity (such as radiation protectors, e.g., Ethyol® or amifostine), radiosensitizers (such as IUdR, BUdR, misonidazole, nimorazole, etanidazole, Fluosol, RSR-13, and motexafin gadolinium (MGd)), hormones (such as thyroid for head and neck cancer), or luteinizing hormone-releasing hormone (LHRH) agonists (also called LHRH analogs or GnRH agonists). Examples of LHRH include, but are not limited to Leuprolide (Lupron, Eligard), Goserelin (Zoladex), Triptorelin (Trelstar) or Histrelin (Vantas).

EMBODIMENTS

The invention provides also the following non-limiting embodiments.

Embodiment 1 is a method of protecting vascular integrity in a subject exposed to a targeted radiation therapy, the method comprising administering to the subject an effective amount of a thrombopoietin (TPO) mimetic.

Embodiment 1(a) is the method of embodiment 1, wherein the TPO mimetic comprises a peptide having the amino acid sequence of SEQ ID NO:1.

Embodiment 1(b) is the method of embodiment 1(a), wherein the peptide has the amino acid sequence of SEQ ID NO:2.

Embodiment 1(c) is the method of embodiment 1(a) or 1(b), wherein the TPO mimetic further comprises a hydrophilic polymer covalently linked to the peptide.

Embodiment 1(d) is the method of embodiment 1(c), wherein the hydrophilic polymer is any one of: i) polyethylene glycol (PEG), ii) polypropylene glycol, iii) polylactic acid, or iv) polyglycolic acid.

Embodiment 1(e) is the method of embodiment 1(d), wherein the hydrophilic polymer is PEG.

Embodiment 1(f) is the method of embodiment 1(e), wherein the PEG is any one of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), or monomethoxypolyethylene glycol-imidazolyl-carbonyl (MePEG-IM).

Embodiment 1(g) is the method of embodiment 1(e), wherein the PEG is methoxypoly(ethylene glycol) (MPEG).

Embodiment 1(h) is the method of embodiment 1(g), wherein the TPO mimetic is RWJ-800088 having a molecular structure of formula (I), or a pharmaceutically acceptable salt or ester thereof:

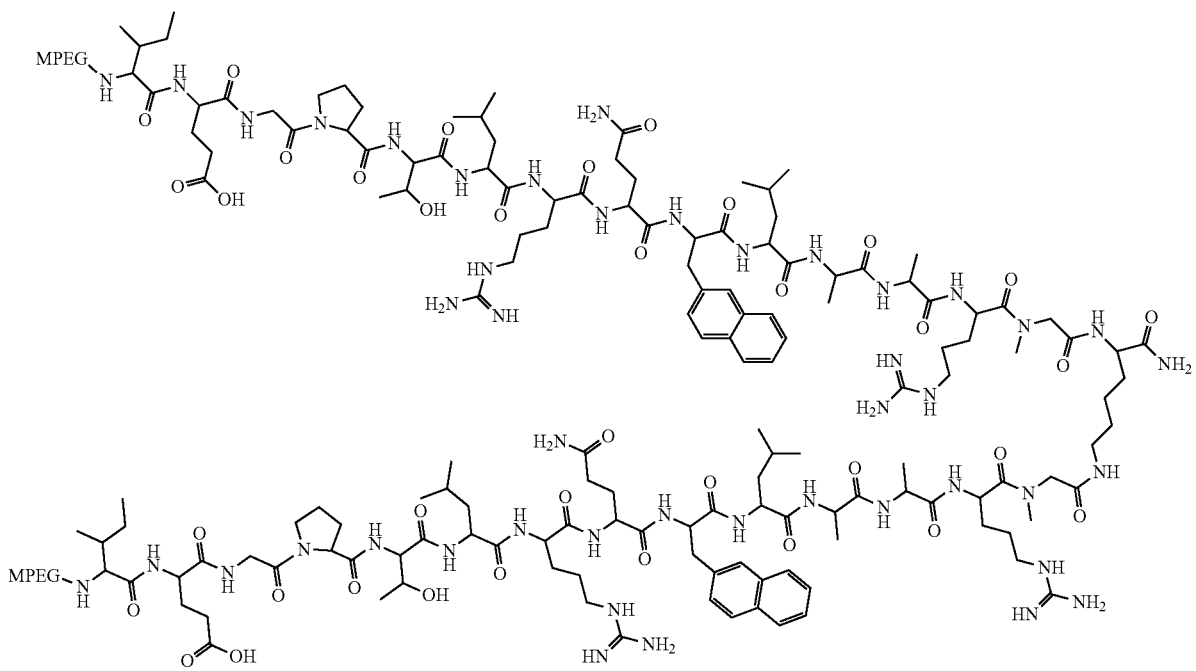

Embodiment 1(i) is the method of embodiment 1(h), wherein the MPEG in the RWJ-800088 is methoxypolyethylene glycol20000.

Embodiment 1(j) is the method of embodiment 1(a), wherein the peptide has the amino acid sequence of SEQ ID NO:3.

Embodiment 1(k) is the method of embodiment 1(j), wherein the peptide is fused to a polypeptide.

Embodiment 1(l) is the method of embodiment 1(k), wherein the polypeptide is a Fc domain.

Embodiment 1(m) is the method of embodiment 1(l), wherein the TPO mimetic is romiplostim.

Embodiment 1(n) is the method of embodiment 1(m), wherein romiplostim comprises the amino acid sequence of SEQ ID NO:4.

Embodiment 2 is the method of any embodiments 1 to 1(n), wherein the subject exposed to the target radiation therapy is being treated for cancer.

Embodiment 2(a) is the method of embodiment 2, wherein the cancer is selected from the group consisting of prostate cancer, head and neck cancer, hepatocellular carcinoma, colon cancer, lung cancer, melanoma, pancreatic cancer, and breast cancer.

Embodiment 2(b) is the method of embodiment 2, wherein the cancer is prostate cancer.

Embodiment 2(c) is the method of embodiment 2, wherein the cancer is head and neck cancer.

Embodiment 3 is the method of any one of embodiments 1 to 2(c), wherein the pharmaceutical composition is administered to the subject at least about 10 minutes to at least about 420 minutes after the subject is administered with the targeted radiation therapy to thereby.

Embodiment 3a is the method of embodiment 3, wherein the TPO mimetic is administered to the subject at least about 20 minutes to at least about 360 minutes after the subject is exposed to the targeted radiation therapy.

Embodiment 4 is the method of embodiment 3, wherein the TPO mimetic is administered to the subject at least about 40 minutes to at least about 240 minutes after the subject is exposed to the targeted radiation therapy.

Embodiment 5 is the method of embodiment 3, wherein the TPO mimetic is administered to the subject at least about 60 minutes to at least about 180 minutes after the subject is exposed to the targeted radiation therapy.

Embodiment 6 is the method of embodiment 3, wherein the TPO mimetic is administered to the subject at about 10 minutes after the subject is exposed to the targeted radiation therapy.

Embodiment 7 is the method of any one of embodiments 1 to 6, wherein the subject is administered more than one dose of the effective amount of the TPO mimetic.

Embodiment 8 is a method of protecting a subject from impaired pudendal artery vasodilation following a targeted radiation therapy, the method comprising administering to the subject in need thereof an effective amount of a thrombopoietin (TPO) mimetic.

Embodiment 9 is a method of reducing vasoconstriction in a subject following a targeted radiation therapy, the method comprising administering to the subject in need thereof an effective amount of a thrombopoietin (TPO) mimetic.

Embodiment 10 is a method of reducing vascular leakage in a subject following a targeted radiation therapy, the method comprising administering to the subject in need thereof an effective amount of a thrombopoietin (TPO) mimetic.

Embodiment 11 is a method of reducing vascular endothelial leukocyte interaction in a subject following a targeted radiation therapy, the method comprising administering to the subject in need thereof an effective amount of a thrombopoietin (TPO) mimetic.

Embodiment 11(a) is the method of any one of embodiments 8 to 11, wherein the TPO mimetic comprises a peptide having the amino acid sequence of SEQ ID NO:1.

Embodiment 11(b) is the method of embodiment 11(a), wherein the peptide has the amino acid sequence of SEQ ID NO:2.

Embodiment 11(c) is the method of embodiment 11(a) or 11(b), wherein the TPO mimetic further comprises a hydrophilic polymer covalently linked to the peptide.

Embodiment 11(d) is the method of embodiment 11(c), wherein the hydrophilic polymer is any one of: i) polyethylene glycol (PEG), ii) polypropylene glycol, iii) polylactic acid, or iv) polyglycolic acid.

Embodiment 11(e) is the method of embodiment 11(d), wherein the hydrophilic polymer is PEG.

Embodiment 11(f) is the method of embodiment 11(e), wherein the PEG is any one of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), or monomethoxypolyethylene glycol-imidazolyl-carbonyl (MePEG-IM).

Embodiment 11(g) is the method of embodiment 11(e), wherein the PEG is methoxypoly(ethylene glycol) (MPEG).

Embodiment 11(h) is the method of embodiment 11(g), wherein the TPO mimetic is RWJ-800088 having a molecular structure of formula (I), or a pharmaceutically acceptable salt or ester thereof:

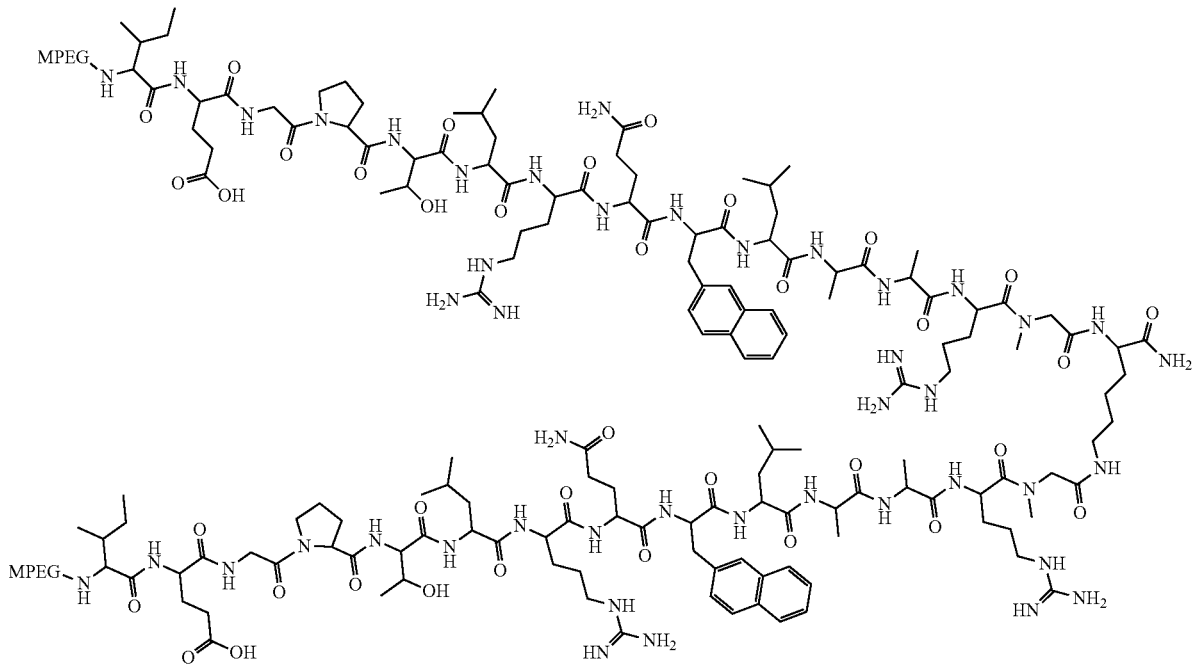

Embodiment 11(i) is the method of embodiment 11(h), wherein the MPEG in the RWJ-800088 is methoxypolyethylene glycol20000.

Embodiment 11(j) is the method of embodiment 11(a), wherein the peptide has the amino acid sequence of SEQ ID NO:3.

Embodiment 11(k) is the method of embodiment 11(j), wherein the peptide is fused to a polypeptide.

Embodiment 11(l) is the method of embodiment 11(k), wherein the polypeptide is a Fc domain.

Embodiment 11(m) is the method of embodiment 11(l), wherein the TPO mimetic is romiplostim.

Embodiment 11(n) is the method of embodiment 11(m), wherein romiplostim comprises the amino acid sequence of SEQ ID NO:4.

Embodiment 12 is the method of any one of embodiments 8 to 11(n), wherein the targeted radiation therapy is administered to the subject to treat a cancer or tumor.

Embodiment 13 is the method of embodiment 12, wherein the cancer is selected from the group consisting of prostate cancer, head and neck cancer, hepatocellular carcinoma, colon cancer, lung cancer, melanoma, pancreatic cancer, and breast cancer.

Embodiment 13(a) is the method of embodiment 13, wherein the cancer is prostate cancer.

Embodiment 13(b) is the method of embodiment 13, wherein the cancer is head and neck cancer.

Embodiment 14 is a method of treating a cancer in a subject in need thereof, comprising administering to the subject a targeted radiation therapy, and an effective amount of a thrombopoietin (TPO) mimetic.

Embodiment 14(a) is the method of embodiment 14, wherein the TPO mimetic comprises a peptide having the amino acid sequence of SEQ ID NO:1.

Embodiment 14(b) is the method of embodiment 14(a), wherein the peptide has the amino acid sequence of SEQ ID NO:2.

Embodiment 14(c) is the method of embodiment 14(a) or 14(b), wherein the TPO mimetic further comprises a hydrophilic polymer covalently linked to the peptide.

Embodiment 14(d) is the method of embodiment 14(c), wherein the hydrophilic polymer is any one of: i) polyethylene glycol (PEG), ii) polypropylene glycol, iii) polylactic acid, or iv) polyglycolic acid.

Embodiment 14(e) is the method of embodiment 14(d), wherein the hydrophilic polymer is PEG.

Embodiment 14(f) is the method of embodiment 14(e), wherein the PEG is any one of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), or monomethoxypolyethylene glycol-imidazolyl-carbonyl (MePEG-IM).

Embodiment 14(g) is the method of embodiment 14(e), wherein the PEG is methoxypoly(ethylene glycol) (MPEG).

Embodiment 14(h) is the method of embodiment 14(g), wherein the TPO mimetic is RWJ-800088 having a molecular structure of formula (I), or a pharmaceutically acceptable salt or ester thereof:

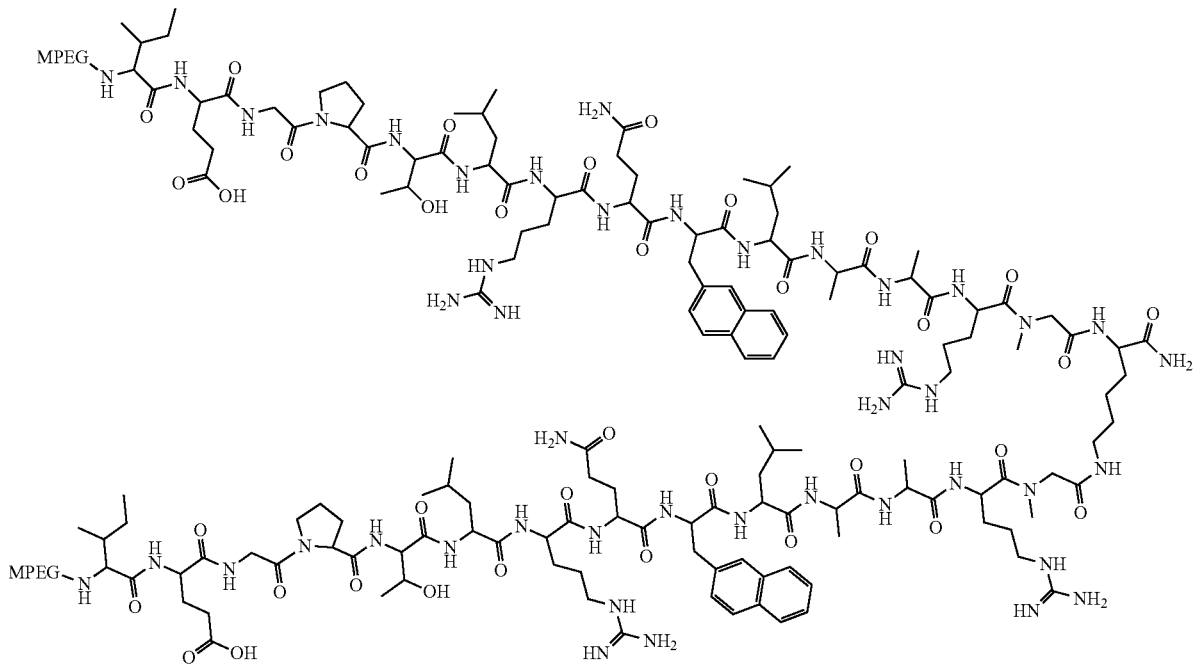

Embodiment 14(i) is the method of embodiment 14(h), wherein the MPEG in the RWJ-800088 is methoxypolyethylene glycol20000.

Embodiment 14(j) is the method of embodiment 14(a), wherein the peptide has the amino acid sequence of SEQ ID NO:3.

Embodiment 14(k) is the method of embodiment 14(j), wherein the peptide is fused to a polypeptide.

Embodiment 14(l) is the method of embodiment 14(k), wherein the polypeptide is a Fc domain.

Embodiment 14(m) is the method of embodiment 14(l), wherein the TPO mimetic is romiplostim.

Embodiment 14(n) is the method of embodiment 14(m), wherein romiplostim comprises the amino acid sequence of SEQ ID NO:4.

Embodiment 15 is the method of any one of embodiment 14 to 14(n), wherein the cancer is selected from the group consisting of prostate cancer, head and neck cancer, hepatocellular carcinoma, colon cancer, lung cancer, melanoma, pancreatic cancer, and breast cancer.

Embodiment 15(a) is the method of embodiment 15, wherein the cancer is prostate cancer.

Embodiment 15(b) is the method of embodiment 15, wherein the cancer is head and neck cancer.

Embodiment 16 is the method of any one of embodiment 14 to 15(b), wherein the TPO mimetic is administered at least about 10 minutes to at least about 420 minutes after the subject is administered with the targeted radiation.

Embodiment 17 is the method of any one of embodiments 14 to 16, wherein the subject is protected from impaired pudendal artery vasodilation following the administration of the targeted radiation therapy and the effective amount of the TPO mimetic.

Embodiment 18 is the method of any one of embodiments 14 to 16, wherein the subject has a reduced vasoconstriction following the administration of the targeted radiation therapy and the effective amount of the TPO mimetic.

Embodiment 19 is the method of any one of embodiments 14 to 16, wherein the subject has a reduced vascular leakage following the targeted radiation therapy and the administration of the effective amount of the TPO mimetic.

Embodiment 20 is the method of any one of embodiments 14 to 16, wherein the subject has a reduced vascular endothelial leukocyte interaction following the targeted radiation therapy and the administration of the effective amount of the TPO mimetic.

Embodiment 21 is a pharmaceutical composition comprising an effective amount of a thrombopoietin (TPO) mimetic and a device and/or another agent for protecting vascular integrity in a subject exposed to a targeted radiation therapy, wherein the TPO mimetic comprises a peptide having the amino acid sequence of SEQ ID NO:1.

Embodiment 22 is a pharmaceutical composition of embodiment 21, wherein the other agent is selected from the group consisting of other TPO mimetics, radiation protectors, radiosensitizers, hormones, or luteinizing hormone-releasing hormone (LHRH) agonists (also called LHRH analogs or GnRH agonists).

Embodiment 22a is the pharmaceutical composition of embodiment 22, wherein the radiation protector comprises Ethyol® (amifostine).

Embodiment 22b is the pharmaceutical composition of embodiment 22 or 22a, wherein the radiosensitizer comprises IUdR, BUdR, misonidazole, nimorazole, etanidazole, Fluosol, RSR-13, or motexafin gadolinium (MGd)).

Embodiment 22c is the pharmaceutical composition of any one of embodiment 22 to 22b, wherein the hormone is thyroid for head and neck cancer treatment.

Embodiment 22d is the pharmaceutical composition of any one of embodiment 22 to 22c, wherein the (LHRH) agonist comprises Leuprolide (Lupron, Eligard), Goserelin (Zoladex), Triptorelin (Trelstar) or Histrelin (Vantas).

Embodiment 23 is the method of any one of embodiments 1-20, wherein the targeted radiation is administered at a dose of 10-70 Gray (Gy).

Embodiment 23(a) is the method of embodiment 23, wherein the dose of the radiation is 10 Gray (Gy).

Embodiment 23(b) is the method of embodiment 23, wherein the dose of the radiation is 20 Gray (Gy).

Embodiment 23(c) is the method of embodiment 23, wherein the dose of the radiation is 30 Gray (Gy).

Embodiment 23(d) is the method of embodiment 23, wherein the dose of the radiation is 40 Gray (Gy).

Embodiment 23(e) is the method of embodiment 23, wherein the dose of the radiation is 50 Gray (Gy).

Embodiment 23(f) is the method of embodiment 23, wherein the dose of the radiation is 60 Gray (Gy).

Embodiment 23(g) is the method of embodiment 23, wherein the dose of the radiation is 70 Gray (Gy).

Embodiment 23(h) is the method of any one of embodiments 23-23(g), wherein the dose of the radiation is administered to the subject in 1 to 10 fractions.

Embodiment 23(i) is the method of any one of embodiments 23-23(h), wherein the subject is treated with the targeted radiation therapy once a day.

Embodiment 23(j) is the method of any one of embodiments 23-23(i), wherein the subject is treated with the targeted radiation therapy twice a day.

Embodiment 24 is the method of any one of embodiments 1-20 and 23-23(j), wherein the targeted radiation is selected from the group consisting of external beam radiation therapy, internal radiation therapy, and systemic radioisotope therapy.

Embodiment 25 is the method of embodiment 24, wherein the targeted radiation is fractioned radiation therapy.

EXAMPLES

Example 1: Administration of a Thrombopoietin Mimetic Preserves Vascular Function in a Rat Prostate Irradiation Model for Erectile Dysfunction Materials and Methods
Animals:

Thirty-five eight-week-old male Sprague Dawley rats were obtained from Charles River Laboratories (Malvern, Pa.) and pair-housed under standard housing conditions. Animals were divided into 4 groups: Saline/Sham, Saline RT, TPOm/Sham, TPOm/RT. All animal work was approved by the Duke University School of Medicine Institutional Animal Care and Use Committee.
TPOm Synthesis and Treatments:

TPOm was synthesized by Janssen Pharmaceuticals as described previously (Knight et al., Int. J. Toxicol. 30(4): 385-404 (2011)), and shipped on dry ice to Duke University as a lyophilized powder. TPOm was reconstituted in sterile saline, sterile filtered, aliquoted, and stored at −20 C until use. TPOm was administered as a single dose via subcutaneous injection (3,000 µg/kg) 10 minutes after RT. This dose was selected based on its effectiveness in rat whole body radiation studies where it produced a substantial survival benefit compared to placebo when administered at multiple time points.
Prostate Irradiation:

Stereotactic image-guided prostate single fraction RT was performed as published previously (Kimura et al., J. Sex Med. 9(6):1535-49 (2012)). In brief, rats were anesthetized and immobilized on a polystyrene block. A CT scan was performed to image the entire pelvis using a GE Discovery RT590 (GE Healthcare, Little Chalfont, UK). Individualized treatment plans were prepared for each rat using the Eclipse treatment planning system (Varian Medical Systems, Palo Alto, CA). The prostate and rectum were contoured, with the primary treatment volume generated by expansion of the prostate by 1 mm followed by subtraction of the rectum expanded by 1 mm. A single, dynamic conformal arc plan using a beam energy of 6 MV was normalized to deliver 20 Gy to 95% of the primary treatment volume in a single fraction with partial sparing of the rectum. The majority of the bladder, the penis and the testes were excluded from the field. The rat was then treated on a NovalisTx radiosurgery linac (Brainlab AG, Munich, DE and Varian Medical Systems) using cone beam computed tomography prior to treatment with bony image guidance within the same anesthesia window as planning. Sham irradiated rats were anesthetized and immobilized on a polystyrene block without irradiation.
Intracavernous Pressure (ICP) Measurements:

For intracavernous pressure (ICP) measurements, a previously published protocol was followed (Kimura et al., J. Sex Med. 8(8):2215-26 (2011)). In brief, rats were anesthetized with ketamine/xylazine. An incision was made in the ventral cervical skin to visualize the carotid artery, and a polyethylene (PE)-50 tubing containing heparinized saline for continuous mean arterial pressure (MAP) monitoring was inserted. The peritoneum was then opened and the testes were retracted. The cavernous nerve along the posterolateral prostate was visualized and a 23G needle connected to saline-filled PE-60 tubing was inserted into the ipsilateral crus near the penile base. Both tubings were connected to a pressure transducer (World Precision Instruments, Sarasota, FL) The cavernous nerve was isolated and stimulated using a bipolar electrode connected to an S48 stimulator (Grass Technologies, West Warwick, RI) with 4, 6 or 8V, for one minute, with a one minute rest between stimulations. MAP and ICP were recorded using LabChart 7 software (ADInstruments, Colorado Spring, CO), and expressed as a ratio to minimize inter-rat differences in baseline pressure and effects of anesthesia.
Ultrasonographic Measurements of Hydralazine-Induced Vasodilation:

Following ICP measurements, acoustic gel was applied to the prostate area and a mouse high frequency echo transducer (MS5505) was applied to the internal pudendal artery. Images were acquired using Vevo 2100 machine (Visual Sonics; Toronto, ON) in B-mode to evaluate arterial diameter by 2-D echocardiography. Reproducible US placement was verified by using the same US-measured distance to the pubic bone in all animals. Hydralazine (Sigma, St. Louis, MO) (0.4 mg/kg) was then infused through the carotid catheter over the course of one minute, and the echocardiography was repeated. Arterial diameter was measured using the vascular package for Vevo 2100 software.
CD31 Staining and Quantification:

Penises were snap-frozen in liquid nitrogen and stored at −80° C. until use. Cryosections (10 µm) were prepared using a Crytome FSE cryostat (ThermoFisher Scientific, Kalamazoo, MI). Sections were fixed for 20 minutes in acetone, air-dried, and blocked with 10% donkey serum (Sigma). Primary antibody (mouse anti-rat CD31, clone TLD-3A12, BD Pharmingen, Franklin Lakes, NJ) and secondary antibody (Alexa Fluor 488-conjugated donkey anti-mouse IgG; Jackson ImmunoResearch, West Grove, PA) were each applied for one hour, and the sections were counterstained with Hoechst 33342 (Sigma) at 2.5 µg/ml for five minutes before fixation in formalin and sealed using Cytosea160 (ThermoScientific). Slides were imaged using a Zeiss Axio Imager microscope equipped with ZEN 2 software. Samples were imaged within 24 hours of staining using the same exposure times across samples. CD31 expression normalized to vessel perimeter was performed using the ImageJ software. First, measurements were globally calibrated to a scale bar of known length (100 microns). Using the ImageJ contouring tool, measurements were then obtained for perimeter (in microns) and area (in microns$^2$). CD31 expression was then quantified by highlighting only the CD31 stained portion surrounding each vessel, and obtaining a pixel count of the stained region, using a uniform threshold across all images. To account for vessel size variation, for each vessel, the raw count for CD31 expression was then normalized to the perimeter for that vessel. All analysis was completed in a blinded manner.

Statistics:

Statistical analysis was completed using Prism 6 (GraphPad, LaJolla, CA). Two-way ANOVAs were used for rate of weight gain and ICP and unpaired t-tests were used to compare histological changes. A Wilcoxon paired-t-test was used to compare arterial diameters in each rat before and after hydralazine administration. Rat weight was assessed using a two-way repeated measures ANOVA.

Results

TPOm Protects Against Reduction in Rate of Weight Gain Following Radiation Therapy (RT).

Figure 1B:
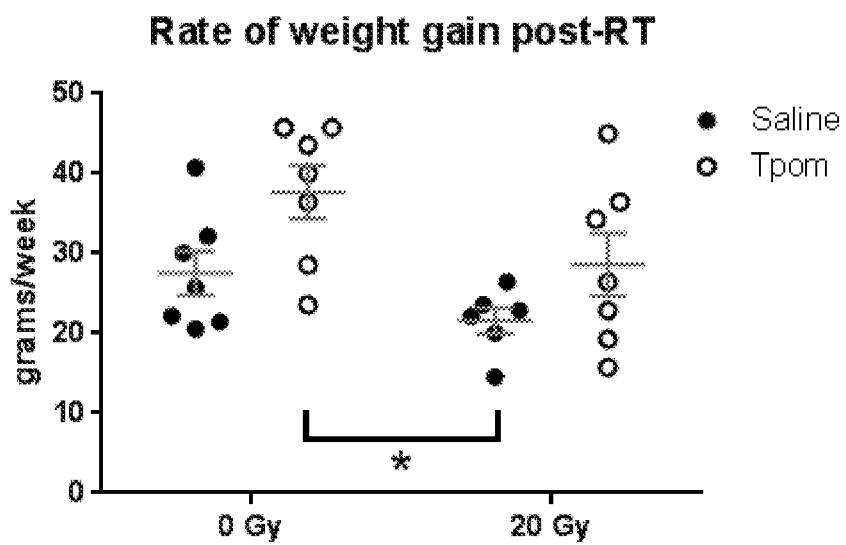
FIG. 1B shows a graph demonstrating that the rate of weight gain (average g/week/rat) was significantly different between groups, with a significant pair-wise difference only between TPOm/sham and saline/RT rats * indicates $p<0.01$. N=8-9 rats/group.

All rats continued to gain weight following RT, which speaks to the precision of the radiation treatment and ability to minimize exposure to the gastrointestinal tissue. However, body weight vs. time plots of saline irradiated rats showed a reduced rate and magnitude of body weight compared to all other treatment groups (FIG. 1A). A two-way repeated measures ANOVA was conducted which demonstrated a significant (p=0.0054) interaction of weight gain, time post-RT and treatment modality. A difference in the mean rate of body weight gain was observed between Saline/Sham (27.5±2.8 g/week), TPOm/sham (37.7±3.3 g/week), Saline/RT (21.6±1.6 g/week) and TPOm/RT (28.6±3.9 g/week) groups (FIG. 1B); however a two-way ANOVA followed by Tukey's post-hoc test, only identified a significant paired difference (p<0.05) between TPOm/Sham and Saline/RT groups only.

TPOm Preserves Arterial Function Following RT.

Figure 2:
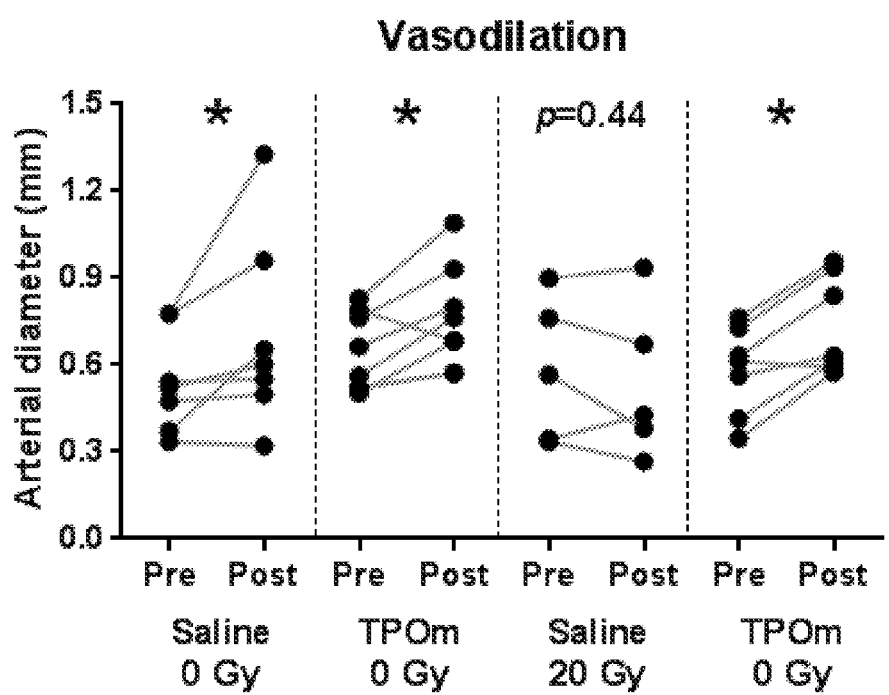
FIG. 2 shows a graph demonstrating that TPOm protected rats from impaired pudendal artery vasodilation following prostate RT. Nine weeks post-RT, the pudendal artery was visualized using echocardiography and the diameter was measured before (Pre) and after (Post) 0.4 mg/kg intravenous hydralazine infusion. * indicates significant (p<0.05) difference between pre-arterial and post-arterial diameters (paired t-test). N=5-8 rats/group.

To assess whether TPOm was able to preserve vascular function, ultrasound echocardiography was used to measure pudendal artery dilation in response to hydralazine administration (FIG. 2). There were no significant differences in baseline arterial diameters across groups with respect to radiation (p=0.86), TPOm, (p=0.47) or interaction (p=0.46). Following hydralazine infusion, arteries from Saline/Sham rats significantly increased in diameter by an average of 28.8%±14.6%. Non-irradiated rats that were treated with TPOm alone showed a 10.4%±10% increase in diameter. Arteries from Saline/RT rats were unable to dilate following hydralazine, showing a non-significant −7.4%±9.9% change in diameter from baseline, indicating that the RT impaired arterial function, e.g., pudendal artery vasodilation, in the rats. However, TPOm treatment following RT preserved arterial function, e.g., protected the rats from impaired pudendal artery vasodilation, with arteries showing a 24.1%±7.2% change in diameter in response to hydralazine, not significantly different than non-irradiated controls.

TPOm Protects Against Vascular Constriction.

Figure 3A:
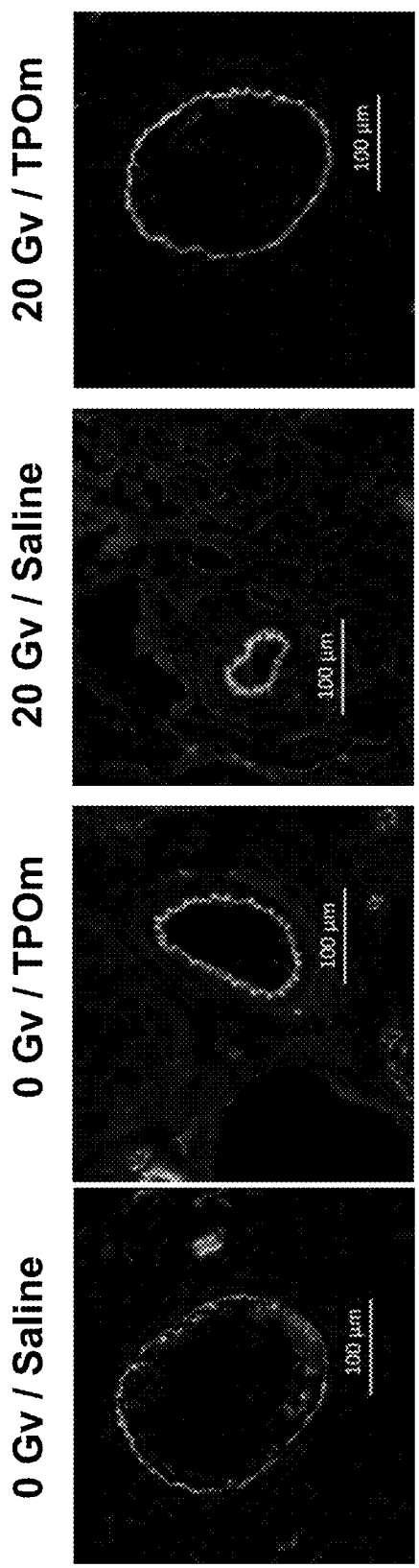
FIG. 3A shows immunofluorescent images of vascular endothelial cells stained for CD31 nine weeks post-RT. To create the immunofluorescent images, penis tissue was excised, cryosectioned, and the vascular endothelial cells were visualized with CD31 immunofluorescence.
Figure 3B:
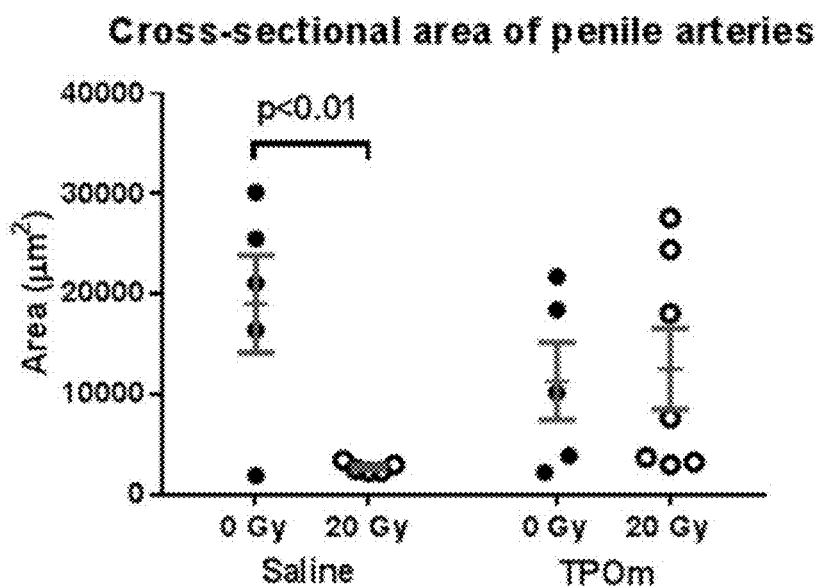
FIG. 3B shows a graph demonstrating the cross-sectional area of penile arteries.
Figure 3C:
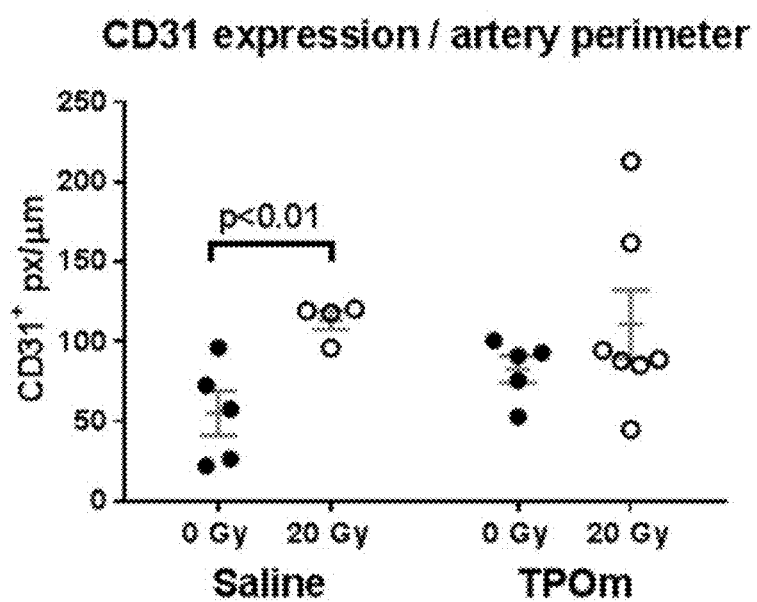
FIG. 3C shows a graph demonstrating the quantification of CD31 density (CD31 expression/artery perimeter) as pixels/micron of perimeter. N=4-6/group.

To assess the effects of RT and TPOm interaction on the penile artery, cryopreserved penises were histologically assessed for CD31 expression to identify the vasculature (FIG. 3A). There were no differences in penile artery perimeter in unirradiated rats that had been treated with saline or TPOm, however radiation significantly decreased the cross-sectional area of the arteries compared to sham/saline controls (p<0.01). This decrease in penile artery cross-sectional area was not seen in the TPOm/RT rats (FIG. 3B), suggesting a protective effect from vasoconstriction induced by RT. CD31 staining (number of CD31$^+$ pixels) was assessed as a marker of vascular endothelial thickness, and this value was normalized to artery perimeter to account for differences in arterial size. When expressed as CD31$^+$ pixels/μm, a two-way ANOVA showed a significant effect of RT, but there were no pair-wise differences in CD31 density between any treatment groups (FIG. 3C).

Vascular Protection by TPOm was not Sufficient to Preserve Erectile Function at 9 Weeks Under the Conditions Tested.

Figure 4:
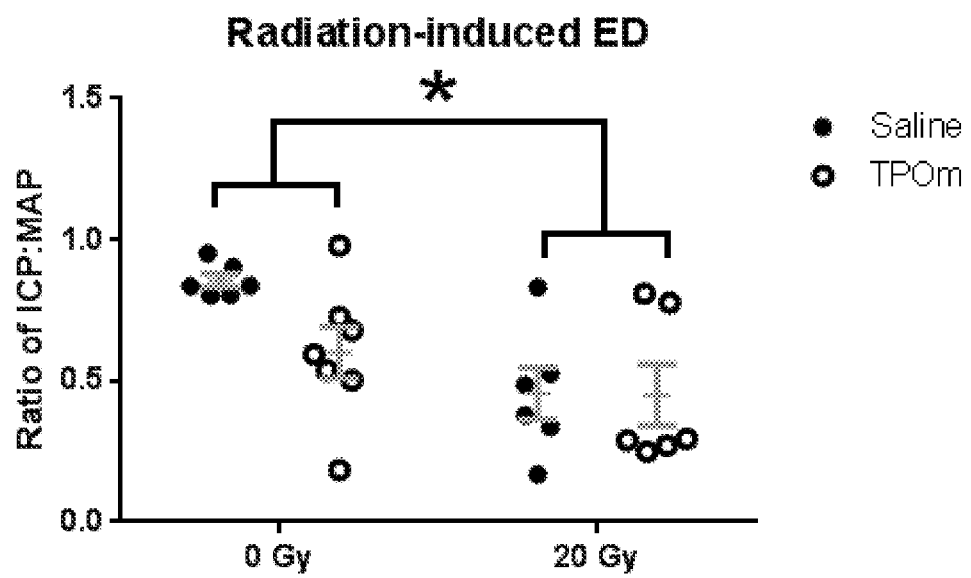
FIG. 4 shows a graph demonstrating that prostate RT (20 Gy) induced erectile dysfunction (ED) in rats was not prevented by a single dose of TPOm administered 10 minutes post RT. Intracavernous pressure (ICP) following cavernous nerve stimulation was tested 9 weeks after RT (20 Gy) and normalized to mean arterial pressure (MAP). Nerves were stimulated with 4V, 6V or 8V, and the best response from each rat was used for the analysis. The asterisk * indicates significant effect of radiation (p=0.004, two-way ANOVA). N=6-7 rats/group.
Figure 5A:
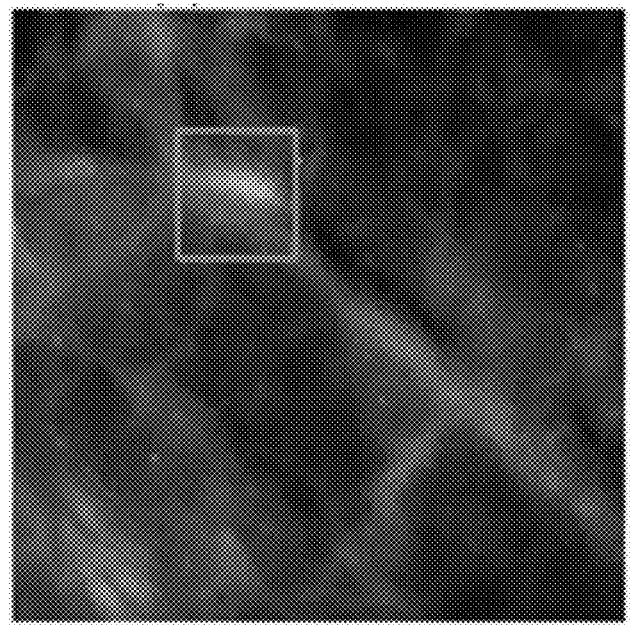
FIG. 5A shows an image of a rectangular region of interest (ROI) selected around vasculature showing expression of dextran at an early time point in the study.
Figure 5B:
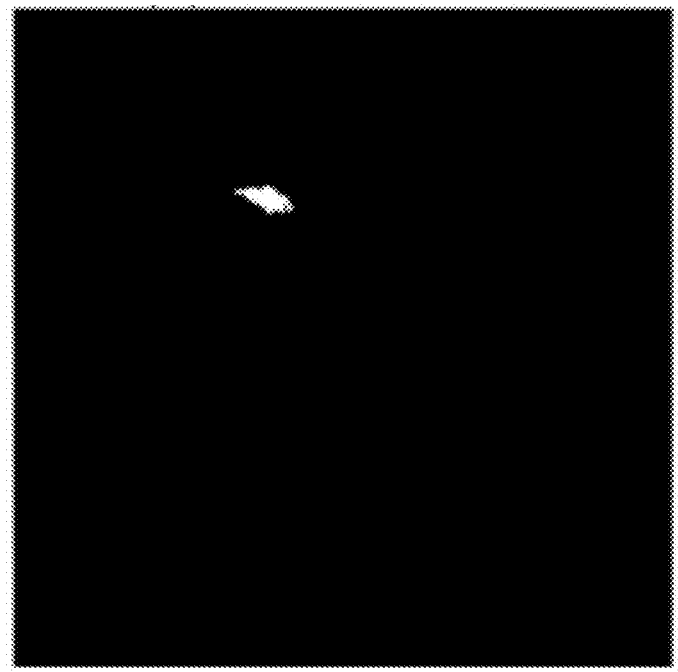
FIG. 5B shows an image of a sub-region of the vasculature identified by thresholding on the $80^{th}$ percentile of the intensity within the ROI in FIG. 5A.
Figure 5C:
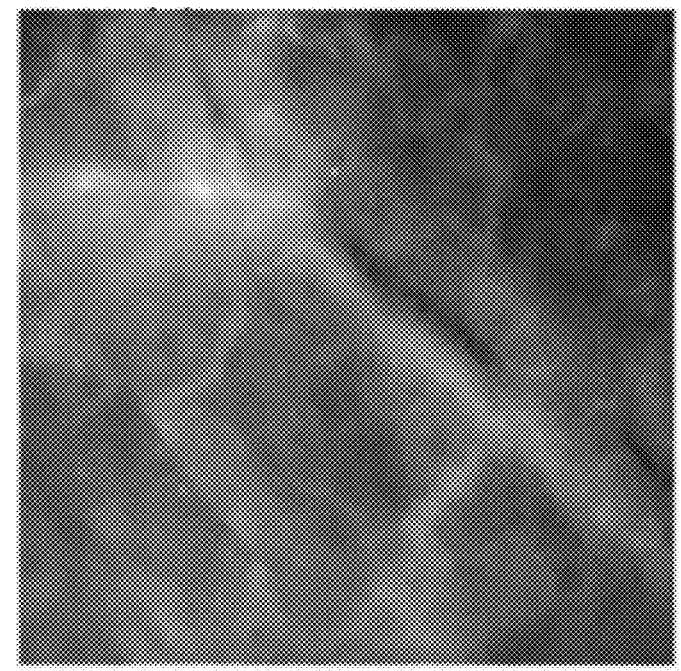
FIG. 5C shows an image of the same field of as in FIG. 5A, seen at the last time point of the study. Notice the enhanced extravascular expression relative to FIG. 5A.
Figure 5D:
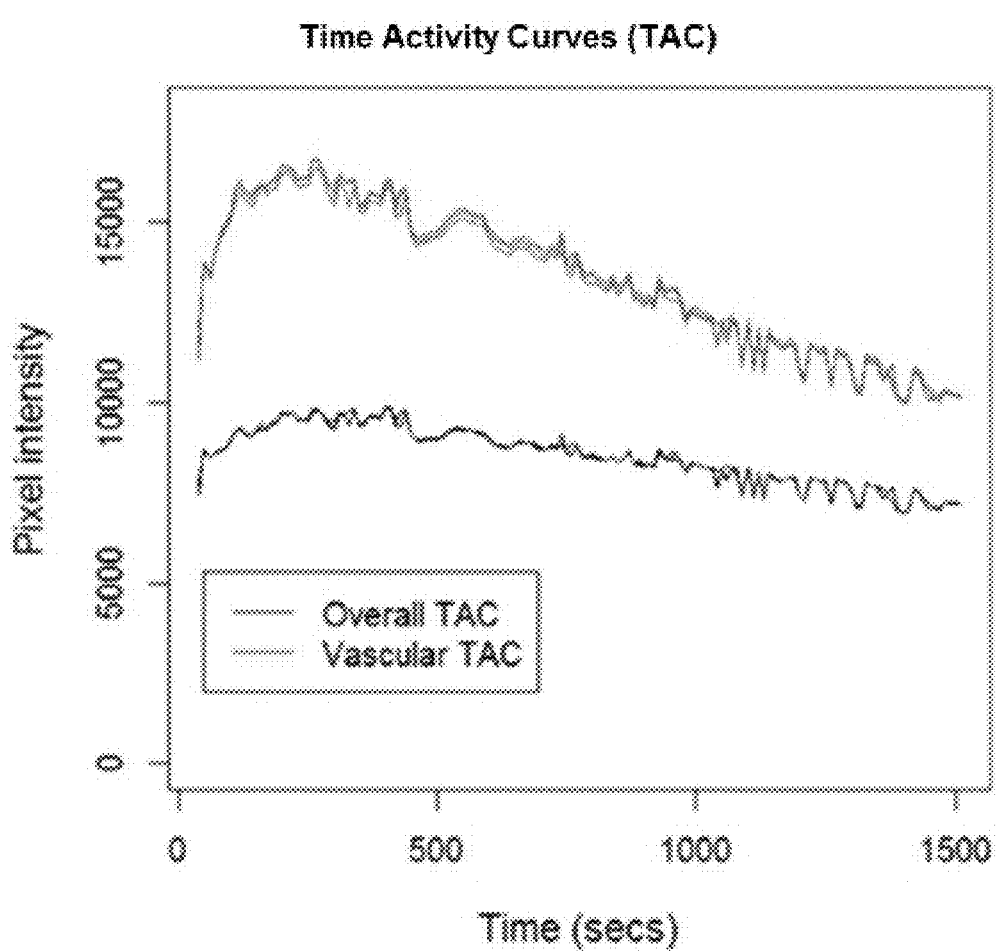
FIG. 5D shows a graph demonstrating the TACs for both the entire field of view or Overall TAC and the vascular TAC or ROI in FIG. 5B, measured at 150 time points, spaced 10 secs apart. Each observation is the average expression over all pixels in the relevant region at that time point. There are three lines for each type of ROI, representing 3 successive slices of tissue. Notice that the vascular TAC (in red) has higher pixel intensity than the overall TAC (in black) at all times.

It has previously been observed that the rat model for radiation-induced ED displays a sigmoidal relationship between radiation dose and incidence of ED (Koontz et al., "Dose dependence of radiation-induced erectile dysfunction in an animal model," J. Sex. Med. 9 (Proceedings from the 17$^{th}$ Annual Fall Scientific Meeting of Sexual Medicine Society of North America, Las Vegas, NV, Nov. 10-13 (2011) (2012)). Doses of 14, 20 and 25 Gy will result in ED in 50%, 80% and 100% of rats, respectively (data not shown). To test the mitigating effects of TPOm, a dose of 20 Gy was applied to detect changes along the sigmoidal portion of the dose response curve. Rats that were treated with TPOm alone showed increased variability of ICP:MAP, but the mean was not significantly different from unirradiated rats treated with saline (FIG. 4). Of the six rats treated with RT alone, five could not produce an ICP:MAP ratio greater than 0.6, showing an ED penetrance of 83% in this study. TPOm treatment following radiation did not prevent ED, with a penetrance of 67%. A two-way ANOVA showed a significant effect of RT (p=0.0043) with post-hoc Tukey's analysis identifying significant differences between unirradiated sham controls and both saline/RT and TPOm/RT rats.

Example 2: Application of a Novel Murine Ear Vein Model to Evaluate the Effects of a Thrombopoietin Mimetic on Radiation-Induced Vascular Permeability and Leukocyte Adhesion Materials and Methods Animals.

Flk1-mCherry mice (Larina et al., Anat. Rec. 292(3):333-41 (2009)) were bred within the Duke University Breeding Core facility. Male and female mice of at least 8 weeks of age were transferred to a non-barrier facility and group housed throughout the experiments. The vascular endothelial cells in Flk1-mCherry mice constitutively express mCherry, which facilitates intravital microscopic imaging and analysis. All animal work was approved by the Duke University School of Medicine Institutional Animal Care and Use Committee.

Ear Irradiation.

Mice were anesthetized with 80/8 mg/kg ketamine/xylazine i.p. injection. Mice were placed in cylindrical lead jigs that shielded the entire body with the exception of the left ear pinna and were irradiated using an Orthovoltage X-ray 320 irradiator (Precision X-ray Inc.; North Branford, CT) at a dose rate of 203 cGy/minute (320 kVp/10 mA with a 2 mm Al filter). All dosimetry was confirmed by Duke Radiation Physics prior to initiation of experiments.

TPOm Synthesis and Administration.

TPOm was synthesized by Janssen Pharmaceuticals as described previously (Knight et al., Int. J. Toxicol. 30(4): 385-404 (2011)), and shipped to Duke University in dried form. TPOm was reconstituted in sterile saline, sterile filtered, aliquoted, and stored at −20° C. until use. Immediately prior to injection, aliquots were thawed and diluted. Mice received 300 μg/kg of TPOm, sub-cutaneously, six hours after radiation.

Intravital Microscopy.

Mice were anesthetized via isoflurane (2%, mixed with oxygen) and the ear was chemically depilated (Nair™) and cleaned with 70% ethanol. The mouse was placed on a heated stage underneath a Zeiss Observer.Z1 (Carl Zeiss AG, Oberkochen, Germany) inverted microscope. The irradiated ear was affixed to a plexi-glass slide using double-sided tape. Images were acquired using Zen Imaging software (Carl Zeiss AG, Oberkochen, Germany). The vascular endothelial cells in Flk1-mCherry mice express mCherry, which was visualized using a Zeiss Texas Red filter (Ex. 560/40; Em. 630/75). Acridine orange and FITC-dextran were visualized using a Zeiss eGFP/FITC/Alexa488 filter (Ex. 470/40; Em. 525/50).

Leukocyte-Endothelial Cell (L/E) Interactions.

After orienting the mouse on the microscope, 0.5 mg of acridine orange (Sigma, St. Louis, MO; dissolved in sterile saline) was injected intravenously. Acridine orange labels all nucleated cells in the blood (i.e., leukocytes). Vasculature was imaged for 60 seconds, with images taken every 200 ms. Rolling leukocytes were defined as cells that marginated along the vessel wall and were clearly dissociated from blood flow. Four venules per mouse were identified, based on their diameter, and the number of leukocytes that rolled past three pre-selected points in each venule were counted. The vessel diameter (D) and free-flowing leukocyte velocities (V) were also measured, and used to calculate shear rate, defined as (8×V)/D. All videos were analyzed by researchers blinded to the treatment groups.

Vascular Permeability Measurement and Assessment.

After orienting the mouse on the microscope, a 30G needle attached to a syringe with Tygon Microbore tubing catheter (Harvard Apparatus) was inserted into the tail vain. Z-stack images of both the FITC and mCherry channels were acquired every 10 seconds, and 0.5 mg of FITC-conjugated 70 kDa dextran injected through the catheter after the third set image of images was collected. Image acquisition was done every 10 seconds for 25 minutes.

A one compartment model of permeability was assumed using the equation for $C_T(t)$. The tissue concentration of dextran in extravascular tissue at time t (known as a time activity curve [TAC]) is given by:

$$\frac{dC_T(t)}{dt} = k_1 C_B(t - \Delta) \quad (0.1)$$

Model (0.1) postulates that the change in tissue concentration at time t is proportional to $C_B(t-\Delta)$, concentration of dextran in the vasculature at a delay $\Delta$. For simplicity, the possibility of dextran returning from extravascular tissue back into the vascular compartment was excluded. In this setting, the quantity of interest is $k_1$, the permeability rate. Assuming the initial condition that $C_B(0)=0$ (there is no dextran in the tissue at time 0), the differential equation (0.1) can be solved as:

$$C_T(t) = k_1 \int_0^t C_B(s - \Delta) ds \quad (0.2)$$

Estimating $k_1$ from equation (0.2) requires knowledge of both the intra and extravascular concentration of dextran at time t, $C_B(t)$ and $C_T(t)$. Due to the lack of a reliable vascular marker, it was difficult to accurately separate the vascular and extravascular components in the images. However, part of the vasculature was able to be identified because the earliest dextran signals are seen only in the vasculature. By drawing an ROI over this region (that TPOm protects vasculature outside of the radiation field. FIG. 3A shows immunofluorescent images of vascular endothelial cells stained for CD31 nine weeks post-RT. To create the immunofluorescent images, penis tissue was excised, cryosectioned, and the vascular endothelial cells were visualized with CD31 immunofluorescence. FIG. 3B shows a graph demonstrating the cross-sectional area of penile arteries. FIG. 3C shows a graph demonstrating the quantification of CD31 density (CD31 expression/artery perimeter) as pixels/micron of perimeter. N=4-6/group.

FIG. 4 shows a graph demonstrating that prostate RT (20 Gy) induced erectile dysfunction (ED) in rats was not prevented by a single dose of TPOm administered 10 minutes post RT. Intracavernous pressure (ICP) following cavernous nerve stimulation was tested 9 weeks after RT (20 Gy) and normalized to mean arterial pressure (MAP). Nerves were stimulated with 4V, 6V or 8V, and the best response from each rat was used for the analysis. The asterisk * indicates significant effect of radiation (p=0.004, two-way ANOVA). N=6-7 rats/group.

Figure), the vascular TAC $C_B(t)$ could be estimated. The assumption that the TAC is uniform through other parts of the vasculature was made. Instead of attempting to identify the extra vascular region, the mean activity over the entire field of view $C_F(t)$, which is composed of both the vascular and tissue components, was computed. Without loss of generality, this overall activity can be expressed, as follows:

$$C_F(t) = v_b C_B(t) + (1 - v_b) C_T(t) \quad (0.3)$$

where $v_b$ is the (unknown) fraction of area in the field of view composed of the vasculature. The unknown tissue TAC $C_T(t)$ in equation (0.3) could then be replaced using equation (0.2), as follows:

$$C_F(t) = v_b C_B(t) + (1 - v_b) k_1 \int_0^t C_B(s - \Delta) ds \quad (0.4)$$

Figure 6:
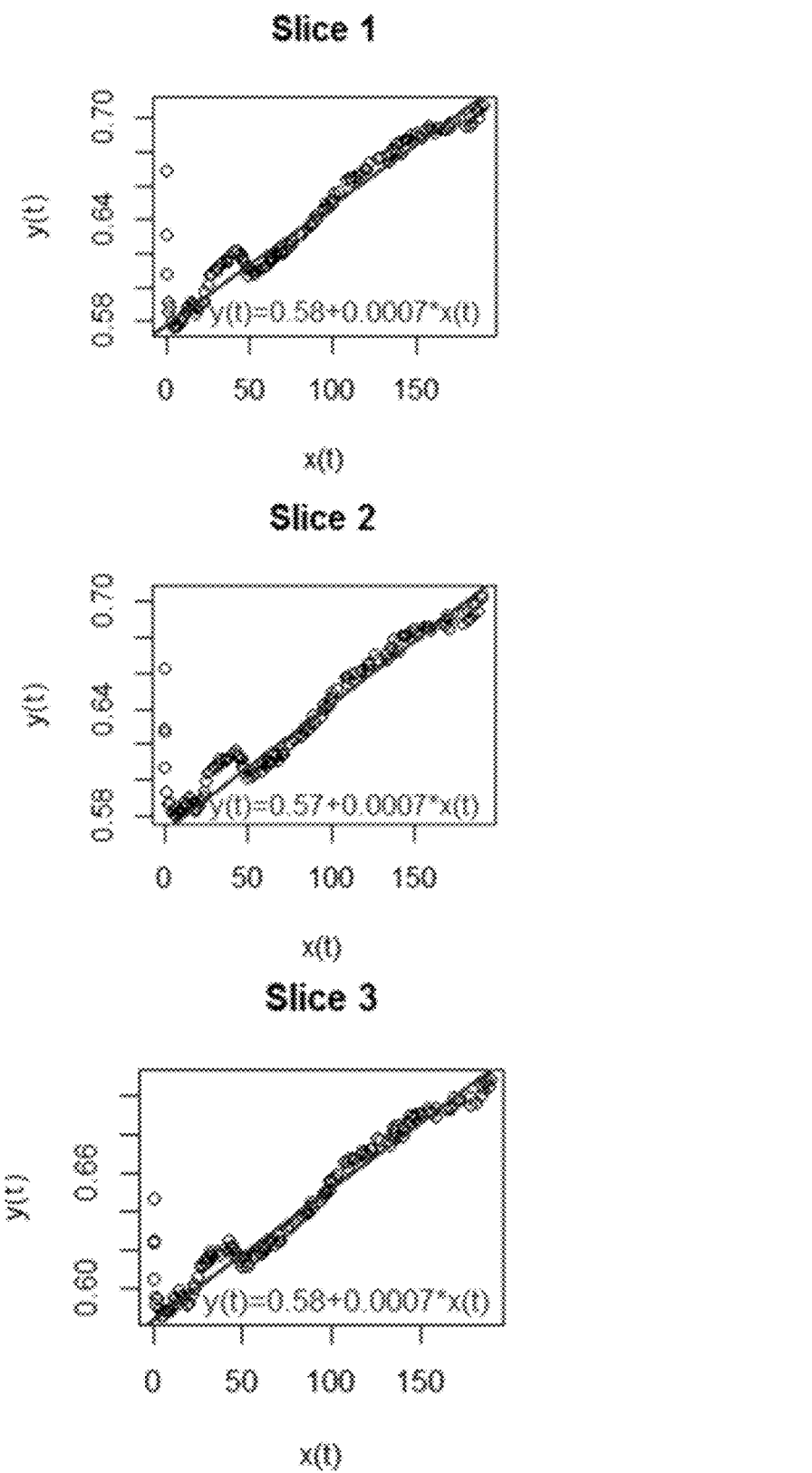
FIG. 6 shows graphs demonstrating the slicewise estimation of permeability rate using Patlak analysis based on the extracted time activity curves (TAC)s for the study shown in FIG. 5. The dots show the observed Patlak plot of the quantities x(t) vs y(t), as given in equation (1.5). The line shows the least squares fit to the data. The equation of the fitted line is given. The permeability rate is estimated from the coefficients of the fitted line. Notice the low variability of estimated coefficients across slices.

Assuming the vascular TAC, $C_B(t)$ to be strictly positive (>0), both sides of (0.4) could be divided by it to obtain a transformed equation:

$$\frac{C_F(t)}{C_B(t)} = v_b + (1 - v_b) k_1 \frac{\int_0^t C_B(s - \Delta) ds}{C_B(t)} \quad (0.5)$$

i.e. $y(t) = v_b + m x(t)$ where $$y(t) = \frac{C_F(t)}{C_B(t)}, \quad x(t) = \frac{\int_0^t C_B(s - \Delta) ds}{C_B(t)}$$

and $m=(1-v_b)k_1$. Equation (0.5) can be seen to be in the form of a straight line, which can be fit using linear regression. The unknown constants $v_b$ and m are estimated as the slope and intercept of the fitted regression line. This estimation technique, usually known as Patlak graphical analysis, is used to estimate rates of tissue transport of radiotracer in dynamic PET studies (Patlak et al., J. Cereb Blood Flow Metab. 3(1):1-7 (1983)). In practice, it takes time for equilibrium to be reached before the linear relationship described in (0.5) results in the slopes shown in FIG. 6. For this reason, the linear relationship was fit by excluding the first 10 minutes of the study. For this purpose, the permeability constant could be estimated as:

$$\hat{k}_1 = \hat{m}/(1-\hat{v}_b).$$

Circulating Blood Cell Analysis.

Mice were euthanized with 50 μL Euthasol (Virbac, Fort Worth, TX) injected intraperitoneally. After mice became non-responsive to toe pinch, but prior to heartbeat cessation, 500 μL of blood was collected by cardiac puncture via heparinized syringe, and immediately vortexed with 20 μL heparin. CBC analysis was conducted using an IDEXX ProCyte Dx Hematology analyzer by the Duke University Veterinary Diagnostic Laboratory.

Results

Effects of TPOm on Vascular Permeability

One of the consequences of radiation-mediated vascular endothelial cell apoptosis is reduced vascular integrity, resulting in vascular leakage (Weintraub et al., Am. Coll. Cardiol. 55(12):1237-9 (2010)). Vascular integrity was assessed by quantifying dextran extravasation from the vasculature following an intravenous injection of 70 kDa FITC-dextran. This size of dextran was selected because it is near the size of albumin; therefore, its extravasation is physiologically relevant (Dreher et al., J. Natl. Cancer Inst. 98(5):335-44 (2006)). Dextran was injected 30 seconds after imaging was initiated, to establish the background signal. Following injection, a strong fluorescent signal was seen within the vasculature, which spread throughout the vascular network. Leakage was observed as "spreading" of FITC signal that originated within the vessels.

Though a model which included reverse transport from the tissue to the vasculature was considered, the standard model with transport in both directions assumes that the blood TAC has a negative exponential shape, implying that the blood TAC monotonically decreases over time. Based on the observed blood TAC presented herein, this is violated in a number of cases, with some individuals increasing, then decreasing, at later times during the imaging. This suggests that the standard model would be a poor fit for some data. The model that was fit is stronger because it uses the empirically observed data without pre-supposing any particular form for the blood TAC.

TPOm Therapy Preserved Vascular Integrity by Reducing Leakage.

Figure 7:
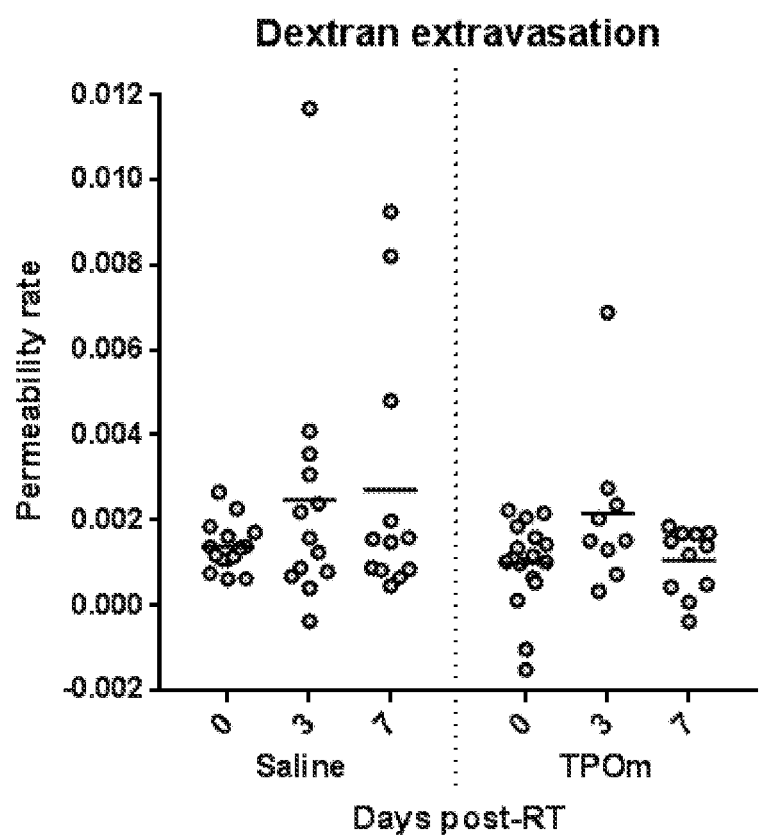
FIG. 7 shows a graph demonstrating the dextran permeability rates at pre-treatment, 3-days and 7-days post-irradiation; saline and TPOm (300 ug/kg) were administered at 6 hours post-irradiation.
Figure 8:
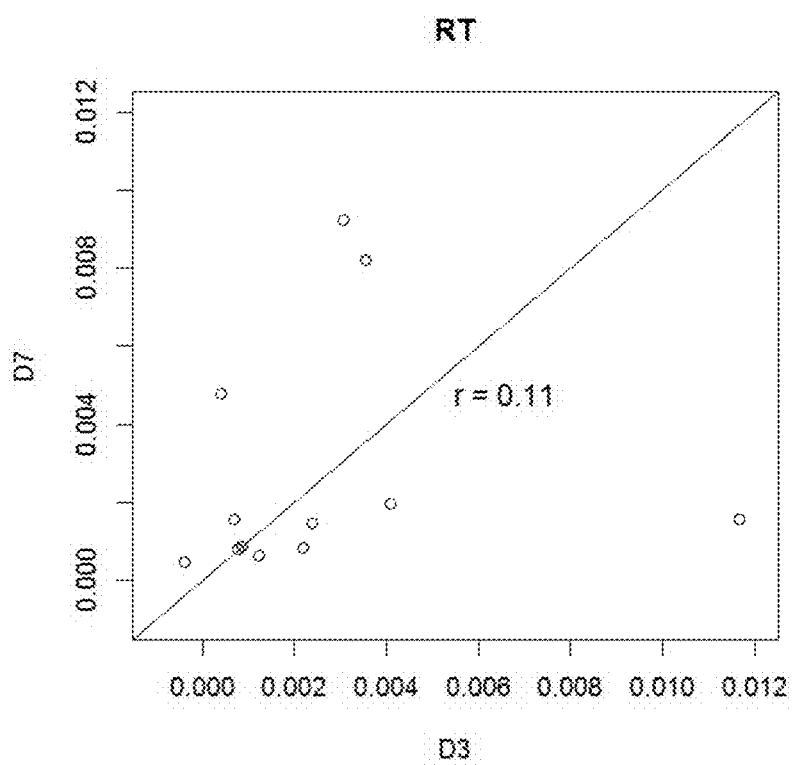
FIG. 8 shows a graph demonstrating that there was no correlation between permeability rates for days 3 and 7 post-RT for individual animals in the Saline/RT group. Each point in the figure is the average estimated permeability value of all slices in a given animal.
Figure 9A:
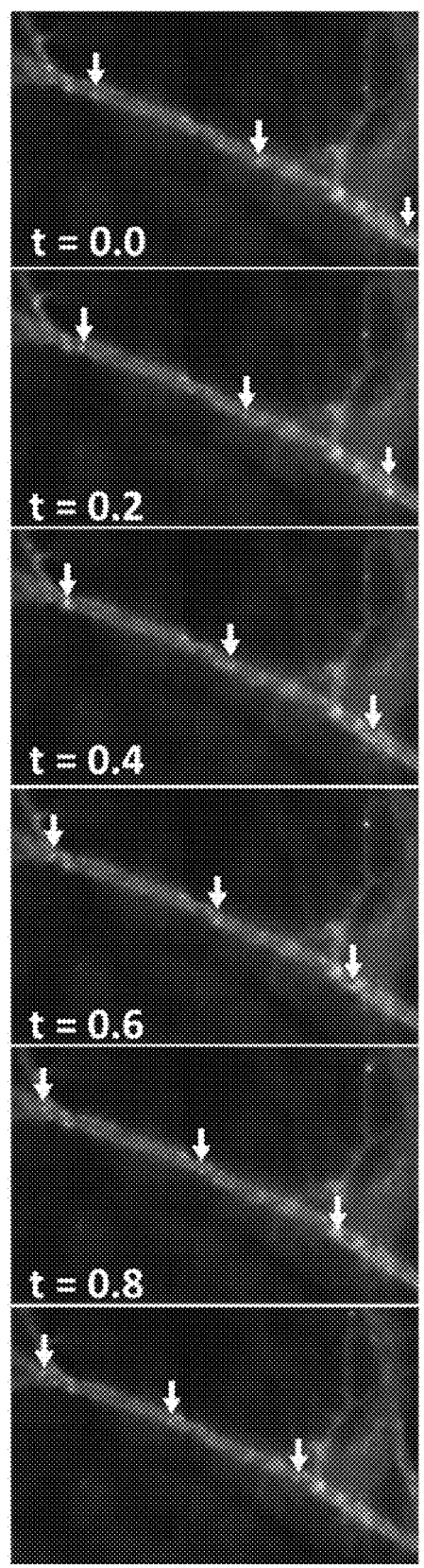
FIG. 9A shows a representative image series showing three marginating leukocytes traveling over the course of 1 second. Leukocytes that rolled along the vascular endothelium were easily distinguished due to their slowed velocity compared to surrounding blood flow.
Figure 9B:
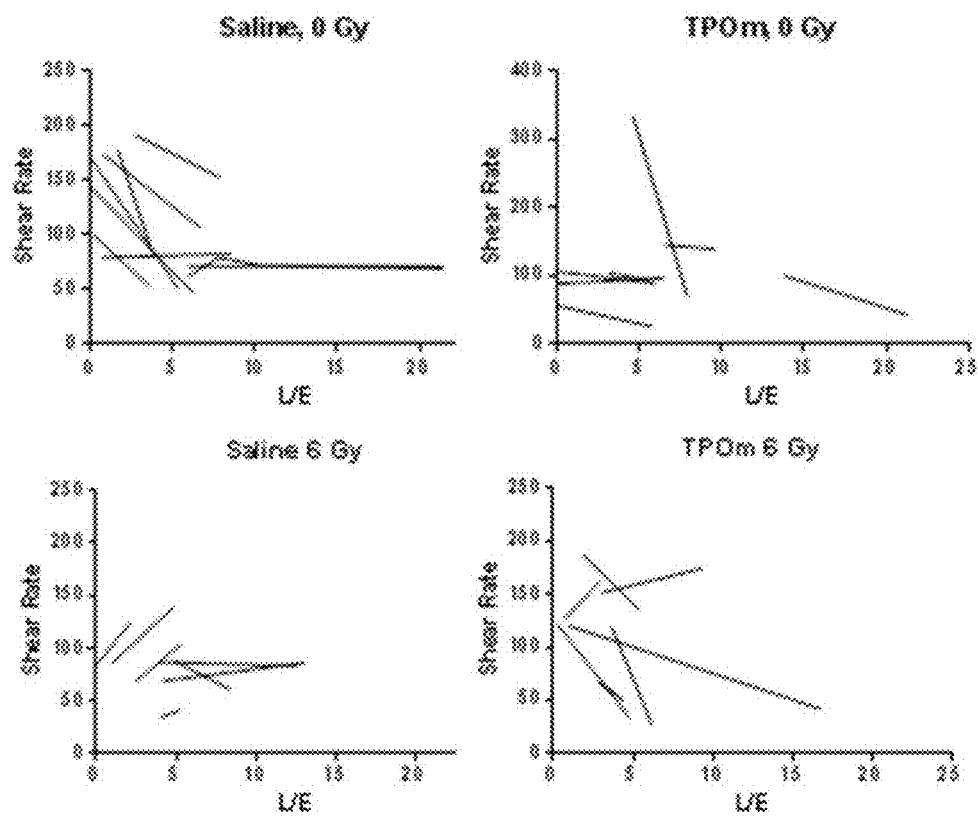
FIG. 9B shows a graph demonstrating plotted shear rates vs. L/E interactions for each mouse and the slope was calculated.
Figure 9C:
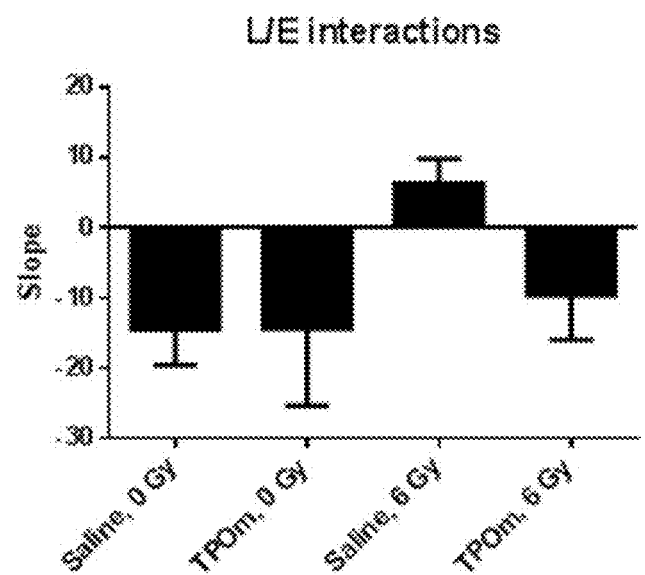
FIG. 9C shows a graph demonstrating that RT significantly altered the relationship between shear rate and L/E interactions, whereas TPOm prevented L/E interaction at higher shear rates.

Non-irradiated control mice showed strong vascular integrity, and the signal remained within the vessels and did not appreciably change over the 25 minute imaging session. In mice where vascular integrity had been compromised by RT, FITC signal clearly extended beyond the vascular mask. Permeability rates were calculated for each mouse and are shown in FIG. 7. Radiation significantly increased permeability rates at days 3 and 7 post-irradiation (p<0.05, compared to controls (Table 1)). However, permeability rates from mice treated with TPOm following radiation were not significantly different from non-irradiated controls at either time point. However, there were some animals that showed elevated permeability in the control group, whereas no animals in the TPOm group did on day 7. There was no correlation between permeability rates at days 3 and 7, suggesting that injury may not peak at the same time amongst animals (FIG. 8).

TABLE 1

ANOVA results of revised dextran permeability rate comparison

| Term | Effect | Std. Error | t-value | p-value |
|---|---|---|---|---|
| Baseline | 0.0012 | 0.0003 | 3.7025 | 0.0003 |
| RT D3 | 0.0013 | 0.0006 | 2.0089 | 0.0483* |
| RT D7 | 0.0015 | 0.0006 | 2.2727 | 0.0260* |
| RT + TPO D3 | 0.0009 | 0.0007 | 1.2689 | 0.2086 |
| RT + TPO D7 | −0.0002 | 0.0007 | −0.2346 | 0.8152 |

Effects of TPOm on Leukocyte-Endothelial Cell Interactions.

Previous studies have utilized intravital microscopy to quantify irradiation-mediated inflammatory responses resulting in increased rolling leukocytes in the terminal venules of irradiated small bowel (Johnson et al., BMC Surgery 4:10 (2004)), skin (Kimura et al., Int. J. Radiat. Oncol. Biol. Phys. 33(3):627-33 (1995)), and sublingual mucosa (Birer et al., "Inhibition of the continuum of radiation-induced normal tissue injury by a redox-active mu porphyrin," Radiation Research, 188(1):94-104 (2017)). To assess leukocyte-endothelial interactions, real-time images of ear vasculature at 24 hours post-irradiation (6 Gy) were obtained. Leukocyte nuclei were labeled following intravascular acridine orange injection, which permitted visualization by fluorescence microscopy. Rolling leukocytes could clearly be seen marginating along the vessel walls, at a rate that was distinctly separated from the free flow.

A) in both sham and RT mice.

Figure 10:
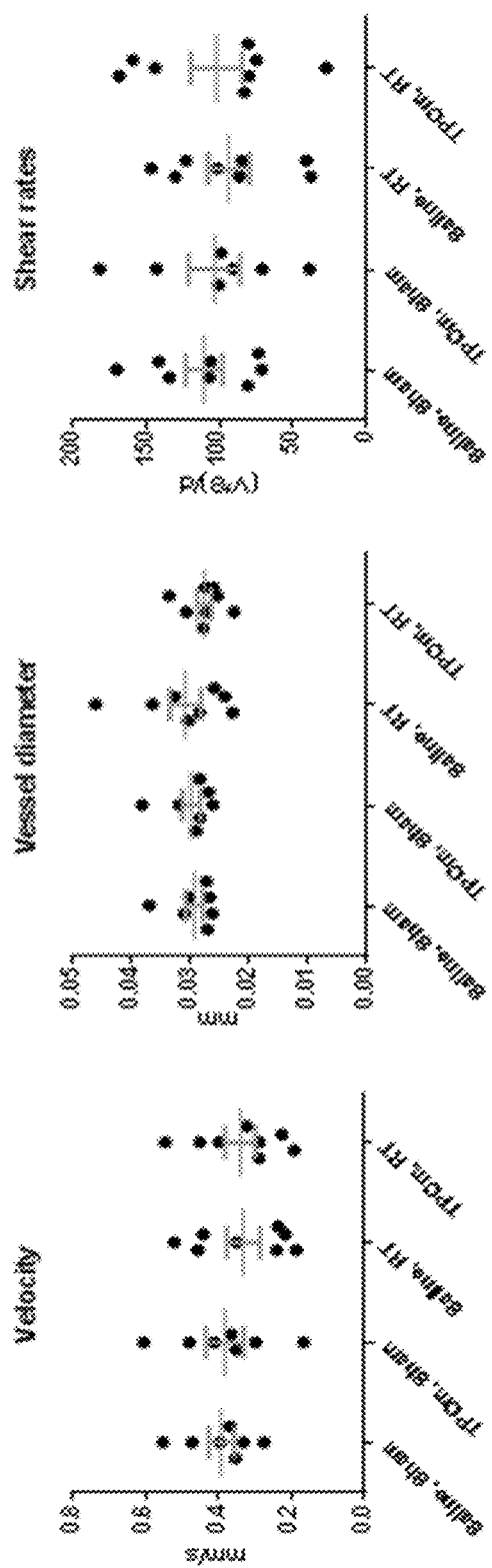
FIG. 10 shows vessel characteristics from acridine orange analysis. Up to four vessels were selected per mouse, and the blood flow velocity and vessel diameter were determined for each. Shear rates were calculated using the equation ((velocity)×(8))/diameter. Each marker represents the average value per mouse, and errors bars represent the mean±SEM. There were no significant differences between treatment groups.

Post-capillary venules were used for analysis, which were distinguished from other vessels based on diameters (approximately 15-60 μm in diameter) and evidence of convergent blood flow. Treatments had no significant effect on average blood flow velocity, diameter or shear rates among the vessels selected. (FIG. 10).

Shear rate, the force of blood flow parallel to vessel walls, has a direct effect on L/E interactions. Higher shear rates reduce leukocyte interactions with adhesion molecules. This translates to fewer L/E interactions at high shear rates and a negative slope when plotting shear rate vs. L/E interactions. To investigate the role of RT on this relationship, shear rates and L/E interactions were determined for at least four vessels per mouse, the values for each vessel were graphed as scatter plots B), and slopes were calculated for each individual mouse using GraphPad Prism. As expected, L/E interactions decreased with increasing shear rates, yielding a slope of −14.4±5.1

C). However, at 24 hours post-irradiation, sufficient endothelial activation had occurred such that L/E interactions persisted, even at higher shear rates, resulting in an average slope of 5.6±3.6.

To rule out the possibility that the observations resulted from systemic changes in leukocyte counts, complete blood counts were performed (Table 2). By 24 hours post-irradiation, there was a slight decrease in platelets in the RT mice, but this was not significant. There were no significant differences in total leukocytes, neutrophils or lymphocytes across groups, or as an effect of RT, TPOm, or the interaction. Therefore, the observed increase in L/E interactions was not merely a byproduct of elevated blood components.

TABLE 2

| | Saline, 0 Gy | TPOm, 0 Gy | Saline, 6 Gy | TPOm, 6 Gy | Effect of TPOm (p-value) | Effect of RT (p-value) | Effect of interaction (p-value) |
|---|---|---|---|---|---|---|---|
| | Complete blood counts were obtained at 24 hours post-RT. | | | | | | |
| Platelets (K/μL) | 582 ± 80 | 531 ± 68 | 370 ± 70 | 548 ± 105 | 0.4523 | 0.2543 | 0.1815 |
| Leukocytes (K/μL) | 2.5 ± 0.5 | 2.55 ± 0.48 | 3.64 ± 0.7 | 2.11 ± 0.33 | 0.2603 | 0.9926 | 0.1073 |
| Neutrophils (K/μL) | 0.368 ± 0.05 | 0.68 ± 0.31 | 0.456 ± 0.09 | 0.232 ± 0.05 | 0.7929 | 0.291 | 0.1235 |
| Lymphocytes (K/μL) | 1.79 ± 0.44 | 1.77 ± 0.23 | 1.52 ± 0.12 | 1.33 ± 0.24 | 0.7046 | 0.2292 | 0.7779 |

N = 5/group; data is presented as means ± SEM

In mice treated with 6 Gy to the ear and administered saline or 300 μg/kg TPOm subcutaneously six hours later, there was a statistically significant effect on the relationship between L/E interactions and shear rate, with an average slope of −14.4±10.9 in the saline group, whereas there was no difference between the TPOm treated group and the non-irradiated controls (average slope of −8.7±6.4). These findings support the hypothesis that TPOm reduces vascular endothelial leukocyte interactions following radiation and therefore may promote maintenance of vascular integrity following irradiation.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. A method of protecting vascular integrity in a subject exposed to a targeted radiation therapy, the method comprising administering to the subject an effective amount of a thrombopoietin (TPO) mimetic comprising the amino acid sequence of SEQ ID NO: 1, wherein the subject is exposed to the targeted radiation at a dose of 10-70 Gray (Gy), and further wherein the targeted radiation therapy is a therapy using ionizing radiation that is preferentially targeted or localized to a specific organ or part of the body.

2. The method of claim 1, wherein the TPO mimetic is RWJ-800088 having the following structure of formula (I), or a pharmaceutically acceptable salt or ester thereof:

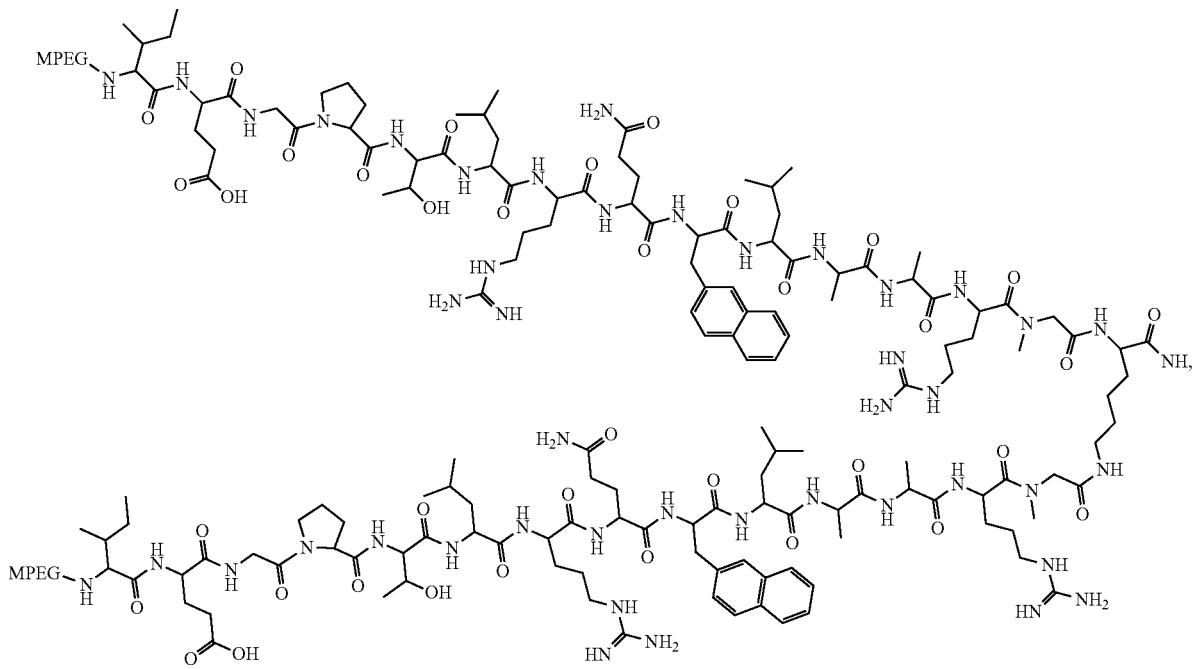

Formula (I)

wherein MPEG represents methoxypolyethyleneglycol20000.

3. The method of claim 1, wherein the subject exposed to targeted radiation therapy is being treated for cancer.

4. The method of claim 3, wherein the cancer is selected from the group consisting of prostate cancer, head and neck cancer, hepatocellular carcinoma, colon cancer, lung cancer, melanoma, pancreatic cancer, and breast cancer.

5. The method of claim 1, wherein the TPO mimetic is administered to the subject at least about 10 minutes to at least about 420 minutes after the subject is exposed to the radiation.

6. The method of claim 5, wherein the TPO mimetic is administered to the subject at least about 20 minutes to at least about 360 minutes after the subject is exposed to radiation.

7. The method of claim 6, wherein the TPO mimetic is administered to the subject at least about 40 minutes to at least about 240 minutes after the subject is exposed to radiation.

8. The method of claim 7, wherein the TPO mimetic is administered to the subject at least about 60 minutes to at least about 180 minutes after the subject is exposed to radiation.

9. The method of claim 1, wherein the subject is protected from impaired pudendal artery vasodilation following the targeted radiation therapy and the administration of the effective amount of the TPO mimetic.

10. The method of claim 1, wherein the subject has a reduced vasoconstriction following the targeted radiation therapy and the administration of the effective amount of the TPO mimetic.

11. The method of claim 1, wherein the subject has a reduced vascular leakage following the targeted radiation therapy and the administration of the effective amount of the TPO mimetic.

12. The method of claim 1, wherein the subject has a reduced vascular endothelial leukocyte interaction following the targeted radiation therapy and the administration of the effective amount of the TPO mimetic.

13. The method of claim 1, wherein the targeted radiation therapy is selected from the group consisting of external beam radiation therapy, internal radiation therapy, and systemic radioisotope therapy, and further wherein the subject is exposed to the targeted radiation at a dose of 20-70 Gy.

14. The method of claim 1, wherein the subject exposed to targeted radiation therapy is being treated for hepatocellular carcinoma.

15. The method of claim 1, wherein the subject exposed to targeted radiation therapy is being treated for prostate cancer.

16. A method of protecting vascular integrity in a subject exposed to a targeted radiation therapy, the method comprising administering to the subject an effective amount of a thrombopoietin (TPO) mimetic comprising the amino acid sequence of SEQ ID NO: 1, wherein the subject exposed to targeted radiation therapy is being treated for a cancer selected from the group consisting of prostate cancer, head and neck cancer, hepatocellular carcinoma, colon cancer, lung cancer, melanoma, pancreatic cancer, and breast cancer, and the TPO mimetic is administered to the subject at least about 10 minutes to at least about 420 minutes after the subject is exposed to the radiation, and wherein the subject is protected from impaired pudendal artery vasodilation, has a reduced vasoconstriction, has a reduced vascular leakage, and/or has a reduced vascular endothelial leukocyte interaction following the targeted radiation therapy and the administration of the effective amount of the TPO mimetic, and further wherein the targeted radiation therapy is a therapy using ionizing radiation that is preferentially targeted or localized to a specific organ or part of the body.

17. The method of claim 16, wherein the TPO mimetic is RWJ-800088having the following structure of formula (I), or a pharmaceutically acceptable salt or ester thereof:

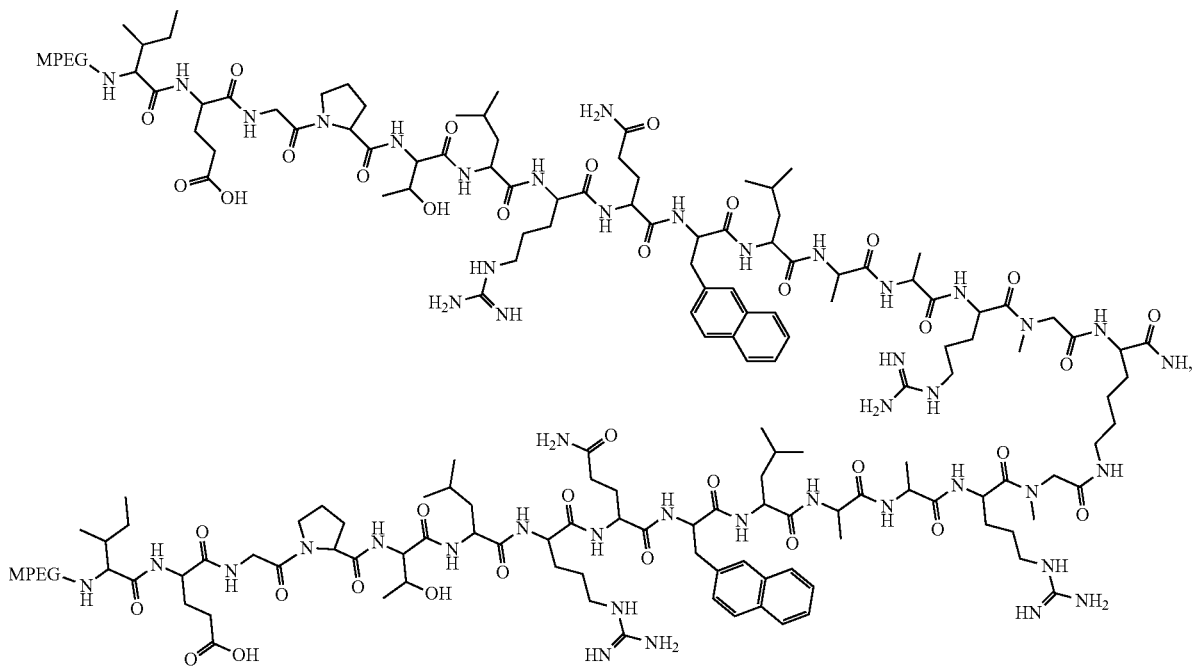

Formula (I)

wherein MPEG represents methoxypolyethyleneglycol20000.

18. The method of claim 16, wherein the targeted radiation therapy is selected from the group consisting of external beam radiation therapy, internal radiation therapy, and systemic radioisotope therapy.

19. The method of claim 16, wherein the targeted radiation is administered at a dose of 10-70 Gray (Gy).

20. A method of protecting vascular integrity in a subject exposed to a targeted radiation therapy, the method comprising administering to the subject an effective amount of a thrombopoietin (TPO) mimetic, wherein the targeted radiation is administered at a dose of 10-70 Gray (Gy) and further wherein the targeted radiation therapy is a therapy using ionizing radiation that is preferentially targeted or localized to a specific organ or part of the body, the TPO mimetic is administered to the subject at least about 10 minutes to at least about 420 minutes after the subject is exposed to the radiation, and the TPO mimetic is RWJ-800088 having the following structure of formula (I), or a pharmaceutically acceptable salt or ester thereof:

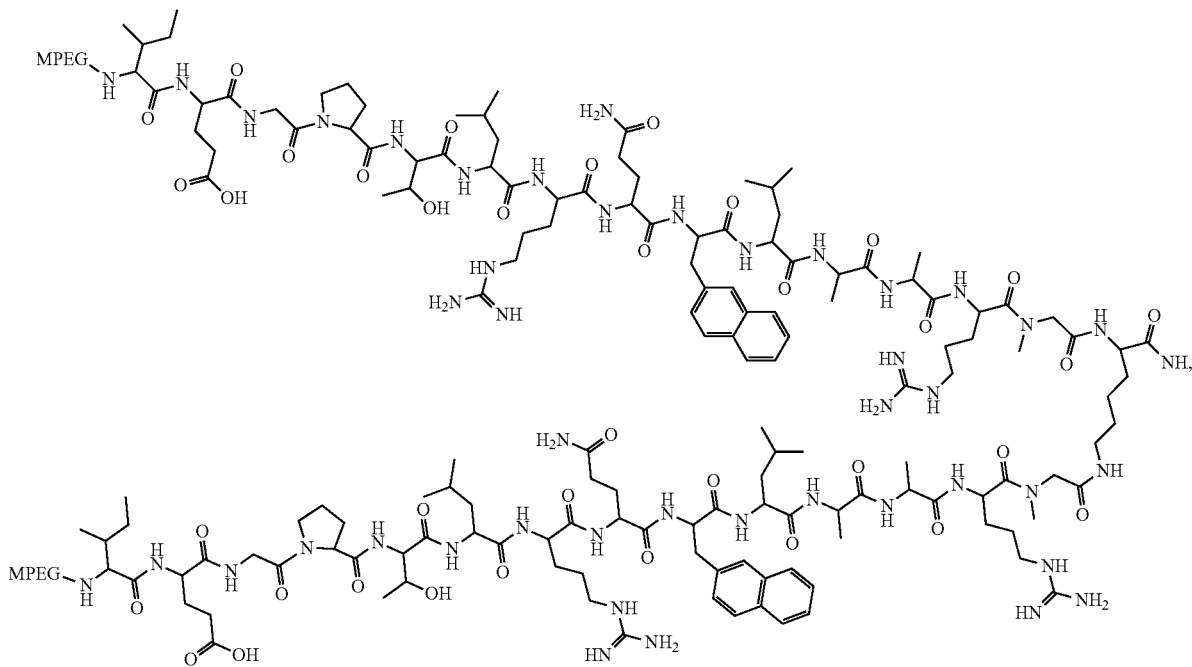

Formula (I)

wherein MPEG represents methoxypolyethyleneglycol20000.

21. The method of claim 20, wherein the subject is protected from impaired pudendal artery vasodilation, has a reduced vasoconstriction, has a reduced vascular leakage, and/or has a reduced vascular endothelial leukocyte interaction following the targeted radiation therapy and the administration of the effective amount of the TPO mimetic.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (9)..(9)
<223> OTHER INFORMATION: tryptophan or beta-(2-naphthyl)alanine
<220> FEATURE:
<221> NAME/KEY: X
<222> LOCATION: (14)..(14)
<223> OTHER INFORMATION: alanine or sarcosine

<400> SEQUENCE: 1

Ile Glu Gly Pro Thr Leu Arg Gln Xaa Leu Ala Ala Arg Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (9)..(9)
<223> OTHER INFORMATION: beta-(2-naphthyl)alanine
<220> FEATURE:
<221> NAME/KEY: X
<222> LOCATION: (14)..(14)
<223> OTHER INFORMATION: sarcosine

<400> SEQUENCE: 2

Ile Glu Gly Pro Thr Leu Arg Gln Xaa Leu Ala Ala Arg Xaa
1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Ile Glu Gly Pro Thr Leu Arg Gln Trp Leu Ala Ala Arg Ala
1               5                   10

<210> SEQ ID NO 4
<211> LENGTH: 269
<212> TYPE: PRT
<213> ORGANISM: Artificial Sequence
<220> FEATURE:
<223> OTHER INFORMATION: Recombinant peptide

<400> SEQUENCE: 4

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ile Glu Gly Pro Thr Leu Arg
225                 230                 235                 240

Gln Trp Leu Ala Ala Arg Ala Gly Gly Gly Gly Gly Gly Gly Ile
                245                 250                 255

Glu Gly Pro Thr Leu Arg Gln Trp Leu Ala Ala Arg Ala
            260                 265
```